US009309209B2

(12) United States Patent
Gilbeau

(10) Patent No.: US 9,309,209 B2
(45) Date of Patent: Apr. 12, 2016

(54) DERIVATIVE OF EPICHLOROHYDRIN OF NATURAL ORIGIN

(75) Inventor: Patrick Gilbeau, Braine-le-Comte (BE)

(73) Assignee: SOLVAY SA, Brussels (BE)

( * ) Notice: Subject to any disclaimer, the term of this patent is extended or adjusted under 35 U.S.C. 154(b) by 112 days.

(21) Appl. No.: 13/876,003

(22) PCT Filed: Sep. 26, 2011

(86) PCT No.: PCT/EP2011/066689
§ 371 (c)(1),
(2), (4) Date: Mar. 26, 2013

(87) PCT Pub. No.: WO2012/041816
PCT Pub. Date: Apr. 5, 2012

(65) Prior Publication Data
US 2013/0184477 A1 Jul. 18, 2013

(30) Foreign Application Priority Data

Sep. 30, 2010 (EP) ..................................... 10183593

(51) Int. Cl.
| C07D 303/00 | (2006.01) |
| C07D 303/08 | (2006.01) |
| C07D 301/26 | (2006.01) |
| C07D 303/16 | (2006.01) |
| C07D 303/18 | (2006.01) |
| C07D 303/40 | (2006.01) |
| C07D 303/46 | (2006.01) |

(52) U.S. Cl.
CPC ............ *C07D 303/08* (2013.01); *C07D 301/26* (2013.01); *C07D 303/16* (2013.01); *C07D 303/18* (2013.01); *C07D 303/40* (2013.01); *C07D 303/46* (2013.01)

(58) Field of Classification Search
CPC .. C07D 301/26; C07D 303/08; C07D 303/46; C07D 303/18; C07D 303/40; C07D 303/16
USPC ....................................................... 549/513
See application file for complete search history.

(56) References Cited

U.S. PATENT DOCUMENTS

| 280,893 | A | 7/1883 | Baujard |
| 855,727 | A | 9/1907 | Queneau |
| 2,060,715 | A | 11/1936 | Arvin |
| 2,063,871 | A | 12/1936 | Dreyfus |
| 2,063,891 | A | 12/1936 | Dreyfus |
| 2,144,612 | A | 1/1939 | Britton et al. |
| 2,198,600 | A | 4/1940 | Britton et al. |
| 2,248,635 | A | 7/1941 | Marple et al. |
| 2,319,876 | A | 5/1943 | Moss |
| 2,444,333 | A | 6/1948 | Castan |
| 2,463,850 | A | 3/1949 | Brooks |
| 2,505,735 | A | 4/1950 | Halbedel |
| 2,726,072 | A | 12/1955 | Herman |
| 2,733,195 | A | 1/1956 | Miller |
| 2,811,227 | A | 10/1957 | O'Connor |
| 2,829,124 | A | 4/1958 | Napravnik et al. |
| 2,860,146 | A | 11/1958 | Furman et al. |
| 2,876,217 | A | 3/1959 | Paschall |
| 2,945,004 | A | 7/1960 | Greenlee |
| 2,960,447 | A | 11/1960 | Anderson et al. |
| 3,026,270 | A | 3/1962 | Robinson, Jr. |
| 3,052,612 | A | 9/1962 | Henegar et al. |
| 3,061,615 | A | 10/1962 | Viriot et al. |
| 3,121,727 | A | 2/1964 | Baliker et al. |
| 3,135,705 | A | 6/1964 | Vandenberg |
| 3,158,580 | A | 11/1964 | Vandenberg |
| 3,158,581 | A | 11/1964 | Vandenberg |
| 3,247,227 | A | 4/1966 | White |
| 3,260,059 | A | 7/1966 | Rosenberg et al. |
| 3,341,491 | A | 9/1967 | Robinson et al. |
| 3,355,511 | A | 11/1967 | Schwarzer |
| 3,385,908 | A | 5/1968 | Schwarzer |
| 3,445,197 | A | 5/1969 | Resh et al. |
| 3,457,282 | A | 7/1969 | Polak et al. |
| 3,618,295 | A | 11/1971 | Geiger et al. |
| 3,711,388 | A | 1/1973 | Gritzner |
| 3,766,221 | A | 10/1973 | Becker |
| 3,839,169 | A | 10/1974 | Moyer |

(Continued)

FOREIGN PATENT DOCUMENTS

| BE | 422877 A | 8/1937 |
| CA | 2375245 A1 | 12/2000 |

(Continued)

OTHER PUBLICATIONS

Medium and Long-term Opportunities and Risks of Biotechnological Production of Bulk Chemicals from renewable Resources—The Potential of White Technology—The BREW project—Final Report—prepared under the European Commission GRXTH Programme (DG Research) Ulrecht, Sep. 2006 (pp. 29-31).
Ullmann's Encyclopedia Industrial Chemistry, $5^{th}$ Ed. vol. A6 (1988) pp. 401-477.
Polymer Science Dictionary, M.S.M., Elsevier Applied Chemistry, London & New York, 1989 p. 86.
Perry's Chemical Engineers' Handbook, $5^{th}$ Edition, 1984, Section 21, pp. 21-55.
M. Schellentrager, "Untersuchungen zur oxidation Entfarbung aus gewahlter Reaktivfarbslotte: Analyse der Abbauprodukte misteels hochauflosender LC-MS", Dissertation. XP 0002548413 (Jan. 1, 2006) w/ English Abstract.
E. Milchert et al., "Installation for the Recovery of Dichloropropanols and Epichlorohydrin from the Waste Water in Epichlorchydrin Production", Pol. J. Appl. Chem., vol. 41, p. 113-118 (1997).

(Continued)

*Primary Examiner* — T. Victor Oh
(74) *Attorney, Agent, or Firm* — Xuping Fu

(57) ABSTRACT

Derivative of epichlorohydrin of natural origin, selected from the group consisting of glycidyl ethers presenting an epoxide equivalent weight higher than or equal to 50 g/equivalent and lower than or equal to 15000 g/equivalent, of glycidyl esters, of glycidyl amides, of glycidyl imides, of glycidyl amines, and of any mixture thereof, and of which the $^{14}C$ mass content is such that the ratio $^{14}C/^{12}C$ is higher than $0.7 \, 10^{-12}$.

17 Claims, No Drawings

(56) References Cited

U.S. PATENT DOCUMENTS

| | | | |
|---|---|---|---|
| 3,865,886 A | 2/1975 | Schindler et al. | |
| 3,867,166 A | 2/1975 | Sullivan | |
| 3,879,180 A | 4/1975 | Hutgens et al. | |
| 3,954,581 A | 5/1976 | Carlin | |
| 3,968,178 A | 7/1976 | Obrecht et al. | |
| 3,980,679 A * | 9/1976 | Becker | 549/517 |
| 4,003,723 A | 1/1977 | Schafer et al. | |
| 4,011,251 A | 3/1977 | Tjurin et al. | |
| 4,024,301 A | 5/1977 | Witenhafer et al. | |
| 4,104,434 A | 8/1978 | Johnson | |
| 4,127,594 A | 11/1978 | Anderson et al. | |
| 4,173,710 A | 11/1979 | Boulet et al. | |
| 4,197,399 A | 4/1980 | Noel et al. | |
| 4,240,885 A | 12/1980 | Suciu et al. | |
| 4,255,470 A | 3/1981 | Cohen et al. | |
| 4,284,573 A * | 8/1981 | Arnett et al. | 549/517 |
| 4,294,776 A | 10/1981 | Hardy et al. | |
| 4,309,394 A | 1/1982 | Hudson | |
| 4,322,367 A | 3/1982 | Silvis | |
| 4,390,680 A | 6/1983 | Nelson | |
| 4,405,465 A | 9/1983 | Moore et al. | |
| 4,464,517 A | 8/1984 | Makino et al. | |
| 4,499,255 A | 2/1985 | Wang et al. | |
| 4,560,812 A | 12/1985 | Blytas | |
| 4,595,469 A | 6/1986 | Foller | |
| 4,599,178 A | 7/1986 | Blytas | |
| 4,609,751 A | 9/1986 | Hajjar | |
| 4,634,784 A | 1/1987 | Nagato et al. | |
| 4,655,879 A | 4/1987 | Brockmann et al. | |
| 4,877,497 A | 10/1989 | Watanabe et al. | |
| 4,898,644 A | 2/1990 | Van Horn | |
| 4,935,220 A | 6/1990 | Schneider et al. | |
| 4,960,953 A | 10/1990 | Jakobson et al. | |
| 4,973,763 A | 11/1990 | Jakobson et al. | |
| 4,990,695 A | 2/1991 | Buenemann et al. | |
| 5,041,688 A | 8/1991 | Jakobson et al. | |
| 5,169,964 A | 12/1992 | Jakobson et al. | |
| 5,200,163 A | 4/1993 | Henkelmann et al. | |
| 5,278,260 A | 1/1994 | Schaffner et al. | |
| 5,286,354 A | 2/1994 | Bard et al. | |
| 5,344,945 A | 9/1994 | Grunchard | |
| 5,359,094 A | 10/1994 | Teles et al. | |
| 5,393,428 A | 2/1995 | Dilla et al. | |
| 5,445,741 A | 8/1995 | Dilla et al. | |
| 5,478,472 A | 12/1995 | Dilla et al. | |
| 5,486,627 A | 1/1996 | Quarderer et al. | |
| 5,567,359 A | 10/1996 | Cassidy et al. | |
| 5,578,740 A | 11/1996 | Au et al. | |
| 5,679,839 A | 10/1997 | Armand et al. | |
| 5,710,350 A | 1/1998 | Jeromin et al. | |
| 5,731,476 A | 3/1998 | Shawl et al. | |
| 5,744,655 A | 4/1998 | Thomas et al. | |
| 5,766,270 A | 6/1998 | Neuman et al. | |
| 5,779,915 A | 7/1998 | Becker et al. | |
| 5,908,946 A | 6/1999 | Stern et al. | |
| 5,955,043 A | 9/1999 | Neuman et al. | |
| 5,993,974 A | 11/1999 | Fukushima et al. | |
| 6,024,839 A | 2/2000 | Schufeldt | |
| 6,103,092 A | 8/2000 | Silva | |
| 6,111,153 A | 8/2000 | Crow et al. | |
| 6,142,458 A | 11/2000 | Howk | |
| 6,177,599 B1 | 1/2001 | Cowfer et al. | |
| 6,270,682 B1 | 8/2001 | Santen et al. | |
| 6,288,248 B1 | 9/2001 | Strebelle et al. | |
| 6,288,287 B2 | 9/2001 | Ueoka et al. | |
| 6,350,888 B1 | 2/2002 | Strebelle et al. | |
| 6,350,922 B1 | 2/2002 | Vosejpka et al. | |
| 6,428,759 B1 | 8/2002 | Smith et al. | |
| 6,521,794 B2 | 2/2003 | Hirota | |
| 6,589,497 B2 | 7/2003 | Smith | |
| 6,719,957 B2 | 4/2004 | Brady, Jr. et al. | |
| 6,740,633 B2 | 5/2004 | Norenberg et al. | |
| 6,806,396 B2 | 10/2004 | Gelblum et al. | |
| 6,831,201 B2 | 12/2004 | Katsuura et al. | |
| 7,126,032 B1 | 10/2006 | Aiken | |
| 7,128,890 B2 | 10/2006 | Ollivier | |
| 7,453,008 B2 | 11/2008 | Ko et al. | |
| 7,557,253 B2 | 7/2009 | Gilbeau | |
| 7,584,629 B2 | 9/2009 | Sohn et al. | |
| 7,615,670 B2 | 11/2009 | Gilbeau | |
| 7,619,056 B2 | 11/2009 | East et al. | |
| 2001/0014763 A1 | 8/2001 | Ueoka et al. | |
| 2004/0016411 A1 | 1/2004 | Joyce et al. | |
| 2004/0024244 A1 | 2/2004 | Walsdorff et al. | |
| 2004/0047781 A1 | 3/2004 | Becenel | |
| 2004/0150123 A1 | 8/2004 | Strofer et al. | |
| 2004/0179987 A1 | 9/2004 | Oku et al. | |
| 2005/0115901 A1 | 6/2005 | Heuser et al. | |
| 2005/0261509 A1 | 11/2005 | Delfort et al. | |
| 2006/0052272 A1 | 3/2006 | Meli et al. | |
| 2006/0079433 A1 | 4/2006 | Hecht et al. | |
| 2006/0123842 A1 | 6/2006 | Sohn et al. | |
| 2007/0112224 A1 | 5/2007 | Krafft et al. | |
| 2007/0170122 A1 | 7/2007 | Tabata et al. | |
| 2007/0251831 A1 | 11/2007 | Kaczur et al. | |
| 2007/0293707 A1 | 12/2007 | Wolfert et al. | |
| 2008/0021209 A1 | 1/2008 | East et al. | |
| 2008/0053836 A1 | 3/2008 | Bulan et al. | |
| 2008/0146753 A1 | 6/2008 | Woike et al. | |
| 2008/0154050 A1 | 6/2008 | Gilbeau | |
| 2008/0161613 A1 | 7/2008 | Krafft et al. | |
| 2008/0194847 A1 | 8/2008 | Krafft et al. | |
| 2008/0194849 A1 | 8/2008 | Krafft et al. | |
| 2008/0194850 A1 | 8/2008 | Krafft et al. | |
| 2008/0194851 A1 | 8/2008 | Gilbeau | |
| 2008/0200642 A1 | 8/2008 | Krafft | |
| 2008/0200701 A1 | 8/2008 | Krafft et al. | |
| 2008/0207930 A1 | 8/2008 | Gilbeau et al. | |
| 2008/0214848 A1 | 9/2008 | Krafft et al. | |
| 2008/0281132 A1 | 11/2008 | Krafft et al. | |
| 2009/0022653 A1 | 1/2009 | Strebelle et al. | |
| 2009/0131631 A1 | 5/2009 | Krafft et al. | |
| 2009/0173636 A1 | 7/2009 | Ooms et al. | |
| 2009/0198041 A1 | 8/2009 | Krafft et al. | |
| 2009/0270588 A1 | 10/2009 | Krafft et al. | |
| 2009/0275726 A1 | 11/2009 | Krafft et al. | |
| 2010/0029959 A1 | 2/2010 | Fan et al. | |
| 2010/0032617 A1 | 2/2010 | Gilbeau et al. | |
| 2010/0105862 A1 | 4/2010 | Krafft et al. | |
| 2010/0105964 A1 | 4/2010 | Krafft et al. | |
| 2010/0168379 A1 | 7/2010 | Krafft et al. | |
| 2010/0170805 A1 | 7/2010 | Krafft et al. | |
| 2010/0179300 A1 | 7/2010 | Boulos et al. | |
| 2010/0179302 A1 | 7/2010 | Krafft et al. | |
| 2010/0212540 A1 | 8/2010 | Bobet et al. | |
| 2010/0294727 A1 | 11/2010 | Gilbeau et al. | |
| 2010/0305271 A1 | 12/2010 | Mentink et al. | |
| 2010/0305367 A1 | 12/2010 | Borremans | |
| 2010/0311874 A1 | 12/2010 | Mentink et al. | |
| 2010/0311905 A1 | 12/2010 | Mentink et al. | |
| 2010/0311942 A1 | 12/2010 | Gilbeau et al. | |
| 2011/0028683 A1 | 2/2011 | Gilbeau et al. | |
| 2011/0086949 A1 | 4/2011 | Mentink et al. | |
| 2011/0118390 A1 | 5/2011 | Feron et al. | |
| 2011/0152545 A1 | 6/2011 | Balthasart et al. | |
| 2011/0166369 A1 | 7/2011 | Krafft et al. | |
| 2011/0195148 A1 | 8/2011 | Mentink et al. | |
| 2011/0237773 A1 | 9/2011 | Gilbeau | |

FOREIGN PATENT DOCUMENTS

| | | |
|---|---|---|
| CN | 1135533 A | 11/1996 |
| CN | 1296003 A | 5/2001 |
| CN | 1583988 A | 2/2005 |
| CN | 101041421 | 9/2007 |
| CN | 101058527 A | 10/2007 |
| DE | 197308 C | 0/1906 |
| DE | 197309 C | 0/1908 |
| DE | 238341 C | 0/1908 |
| DE | 58396 C | 8/1891 |
| DE | 180668 C | 1/1906 |
| DE | 869193 | 3/1953 |
| DE | 955233 A | 1/1957 |
| DE | 1041488 B | 10/1958 |

(56) References Cited

FOREIGN PATENT DOCUMENTS

| | | | |
|---|---|---|---|
| DE | 1075103 | B | 2/1960 |
| DE | 1226554 | B | 10/1966 |
| DE | 2 241 393 | | 2/1974 |
| DE | 25 21 813 | | 12/1975 |
| DE | 3003819 | A1 | 8/1981 |
| DE | 3243617 | | 5/1984 |
| DE | 216471 | A1 | 12/1984 |
| DE | 3721003 | C1 | 12/1988 |
| DE | 4302306 | | 8/1994 |
| DE | 4335311 | A1 | 4/1995 |
| DE | 10203914 | C1 | 10/2003 |
| DE | 10254709 | A1 | 6/2004 |
| EP | 0 296 341 | | 12/1988 |
| EP | 0317184 | A2 | 5/1989 |
| EP | 0317185 | A2 | 5/1989 |
| EP | 0347618 | A2 | 12/1989 |
| EP | 0358255 | A1 | 3/1990 |
| EP | 0421379 | A1 | 4/1991 |
| EP | 0 452 265 | | 10/1991 |
| EP | 0518765 | A1 | 12/1992 |
| EP | 0522362 | A1 | 1/1993 |
| EP | 0535949 | B1 | 4/1993 |
| EP | 0561441 | A1 | 9/1993 |
| EP | 0563720 | A1 | 10/1993 |
| EP | 0582201 | A2 | 2/1994 |
| EP | 0618170 | | 10/1994 |
| EP | 0 916 624 | | 5/1999 |
| EP | 0919551 | A1 | 6/1999 |
| EP | 0774450 | | 2/2000 |
| EP | 0979671 | A1 | 2/2000 |
| EP | 1059278 | A2 | 12/2000 |
| EP | 1153887 | A2 | 11/2001 |
| EP | 1163946 | A1 | 12/2001 |
| EP | 1231189 | A1 | 8/2002 |
| EP | 1298154 | A1 | 4/2003 |
| EP | 1411027 | A1 | 4/2004 |
| EP | 1752435 | A1 | 2/2007 |
| EP | 1752436 | A1 | 2/2007 |
| EP | 1760060 | A1 | 3/2007 |
| EP | 1762556 | A1 | 3/2007 |
| EP | 1770081 | A1 | 4/2007 |
| EP | 1772446 | A1 | 4/2007 |
| EP | 1775278 | A1 | 4/2007 |
| EP | 2085364 | | 8/2009 |
| EP | 2085364 | A1 | 8/2009 |
| FR | 1056360 | A | 2/1954 |
| FR | 1 306 231 | | 10/1961 |
| FR | 1 417 388 | | 10/1964 |
| FR | 1 577 792 | | 8/1965 |
| FR | 1476073 | A | 4/1967 |
| FR | 2151107 | | 4/1973 |
| FR | 2180138 | | 5/1973 |
| FR | 2 217 372 | | 2/1974 |
| FR | 2565229 | A1 | 12/1985 |
| FR | 2752242 | A1 | 2/1998 |
| FR | 2862644 | A1 | 5/2005 |
| FR | 2868419 | A1 | 10/2005 |
| FR | 2869612 | A1 | 11/2005 |
| FR | 2869613 | A1 | 11/2005 |
| FR | 2872504 | A1 | 1/2006 |
| FR | 2881732 | A1 | 8/2006 |
| FR | 2885903 | A1 | 11/2006 |
| FR | 2 912 743 | | 8/2008 |
| FR | 2913683 | | 9/2008 |
| FR | 2913683 | A1 | 9/2008 |
| FR | 2917411 | | 12/2008 |
| FR | 2918058 | A1 | 1/2009 |
| FR | 2925045 | A1 | 6/2009 |
| FR | 2927083 | A1 | 8/2009 |
| FR | 2929611 | A1 | 10/2009 |
| FR | 2935699 | A1 | 3/2010 |
| FR | 2935968 | A1 | 3/2010 |
| GB | 14767 | A | 0/1914 |
| GB | 406345 | | 8/1932 |
| GB | 404938 | A | 1/1934 |
| GB | 467481 | A | 6/1937 |
| GB | 541357 | A | 11/1941 |
| GB | 1459264 | A | 12/1946 |
| GB | 679536 | A | 9/1952 |
| GB | 702143 | A | 1/1954 |
| GB | 724222 | A | 2/1955 |
| GB | 736641 | A | 9/1955 |
| GB | 758665 | A | 10/1956 |
| GB | 799567 | A | 8/1958 |
| GB | 984446 | A | 2/1965 |
| GB | 984633 | A | 3/1965 |
| GB | 1046521 | A | 10/1966 |
| GB | 1083594 | A | 9/1967 |
| GB | 1286893 | A | 8/1972 |
| GB | 1387668 | A | 3/1975 |
| GB | 1 493 538 | | 4/1975 |
| GB | 1414976 | A | 11/1975 |
| GB | 2173496 | A | 10/1986 |
| HU | 2002-003023 | | 3/2004 |
| JP | 3927230 | B2 | 11/1939 |
| JP | 50-062909 | | 5/1975 |
| JP | 21021635 | B | 7/1976 |
| JP | 55041858 | A | 3/1980 |
| JP | 5629572 | | 3/1981 |
| JP | 5699432 | | 8/1981 |
| JP | 56-155009 | A | 12/1981 |
| JP | 60-258171 | A | 12/1985 |
| JP | 61-044833 | A | 3/1986 |
| JP | 61 112066 | A | 5/1986 |
| JP | 61-120688 | A | 6/1986 |
| JP | 61-140532 | A | 6/1986 |
| JP | 61236749 | A | 10/1986 |
| JP | 62242638 | A | 10/1987 |
| JP | 62-278290 | A | 12/1987 |
| JP | 63195288 | A | 8/1988 |
| JP | 2-137704 | | 5/1990 |
| JP | 03014527 | A | 1/1991 |
| JP | 03223267 | A | 10/1991 |
| JP | 3223267 | A | 10/1991 |
| JP | 04089440 | A | 3/1992 |
| JP | 04-217637 | | 8/1992 |
| JP | 6-9589 | A | 1/1994 |
| JP | 625196 | B2 | 4/1994 |
| JP | 06184024 | A | 7/1994 |
| JP | 6321852 | A | 11/1994 |
| JP | 08-003067 | A | 1/1996 |
| JP | 859593 | | 3/1996 |
| JP | 09-2999953 | | 11/1997 |
| JP | 10139700 | A | 5/1998 |
| JP | 10218810 | A | 8/1998 |
| JP | 1998218810 | A | 8/1998 |
| JP | 11012208 | A | 1/1999 |
| JP | 20000344692 | A | 12/2000 |
| JP | 2001-037469 | | 2/2001 |
| JP | 2001-213827 | A | 8/2001 |
| JP | 2001-261308 | | 9/2001 |
| JP | 2001-1261581 | A | 9/2001 |
| JP | 2001276572 | | 10/2001 |
| JP | 20020038195 | A | 2/2002 |
| JP | 2002-256494 | A | 9/2002 |
| JP | 20020265986 | A | 9/2002 |
| JP | 2002-363153 | | 12/2002 |
| JP | 2003-502154 | A | 1/2003 |
| JP | 2003-89680 | A | 3/2003 |
| JP | 2003081891 | A | 3/2003 |
| JP | 2003183191 | A | 7/2003 |
| JP | 2003206473 | A | 7/2003 |
| JP | 2004-130263 | A | 4/2004 |
| JP | 2004518102 | A | 6/2004 |
| JP | 2004216246 | A | 8/2004 |
| JP | 2005007841 | A2 | 1/2005 |
| JP | 2005097177 | A2 | 4/2005 |
| JP | 2005513064 | A | 5/2005 |
| JP | 2005-154292 | A | 6/2005 |
| JP | 2006-52434 | A | 2/2006 |
| JP | 2007-008896 | | 1/2007 |
| JP | 2007-185578 | A | 7/2007 |
| JP | 2002-02033 | A2 | 1/2009 |
| JP | 2009-263336 | | 11/2009 |

(56) References Cited

FOREIGN PATENT DOCUMENTS

| | | |
|---|---|---|
| KR | 900006513 | 11/1987 |
| KR | 1019920003099 B1 | 4/1992 |
| KR | 10-514819 B1 | 9/2005 |
| PL | 136598 | 3/1986 |
| PL | 162910 | 1/1994 |
| SU | 123153 | 1/1959 |
| SU | 1159716 | 6/1965 |
| SU | 1125226 | 11/1984 |
| SU | 1685969 | 10/1991 |
| WF | WO 2006106155 A1 | 10/2006 |
| WO | WO 95/14635 A1 | 6/1995 |
| WO | WO 95/14639 | 6/1995 |
| WO | WO 96/07617 | 3/1996 |
| WO | WO 96/15980 | 5/1996 |
| WO | WO 97/48667 | 12/1997 |
| WO | WO 98/37024 | 8/1998 |
| WO | WO 99/14208 | 3/1999 |
| WO | WO 9932397 A1 | 7/1999 |
| WO | WO 0024674 A1 | 5/2000 |
| WO | WO 01/43762 A2 | 6/2001 |
| WO | WO 0141919 A1 | 6/2001 |
| WO | WO 0186220 A2 | 11/2001 |
| WO | WO 02/26672 A2 | 4/2002 |
| WO | WO 02059536 A1 | 8/2002 |
| WO | WO 03/064357 | 8/2003 |
| WO | WO 2004/065758 | 7/2004 |
| WO | WO 2005021476 A1 | 3/2005 |
| WO | WO 2005054167 A1 | 6/2005 |
| WO | WO 2005/075189 A2 | 8/2005 |
| WO | WO 2005/097722 | 10/2005 |
| WO | WO 2005/115954 | 12/2005 |
| WO | WO 2005/116004 | 12/2005 |
| WO | WO 2006020234 A1 | 2/2006 |
| WO | WO 2006100311 A2 | 9/2006 |
| WO | WO 2006100312 A2 | 9/2006 |
| WO | WO 2006100313 A2 | 9/2006 |
| WO | WO 2006100314 A1 | 9/2006 |
| WO | WO 2006100315 A2 | 9/2006 |
| WO | WO 2006100316 A1 | 9/2006 |
| WO | WO 2006100317 A1 | 9/2006 |
| WO | WO 2006100318 A2 | 9/2006 |
| WO | WO 2006100319 A1 | 9/2006 |
| WO | WO 2006100320 A2 | 9/2006 |
| WO | WO 2006106153 A2 | 10/2006 |
| WO | WO 2006106154 A1 | 10/2006 |
| WO | WO 2007054505 A2 | 5/2007 |
| WO | WO2007/144335 | 12/2007 |
| WO | WO 2008/101866 | 8/2008 |
| WO | WO2008/107468 | 9/2008 |
| WO | WO 2008/110588 | 9/2008 |
| WO | WO2006/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO2009/000773 | 12/2008 |
| WO | WO 2008152043 A1 | 12/2008 |
| WO | WO 2009/016149 A2 | 2/2009 |
| WO | WO 2009026212 A1 | 2/2009 |
| WO | WO2009/043796 A1 | 4/2009 |
| WO | WO 2009/077528 | 6/2009 |
| WO | WO 2009/077528 A1 | 6/2009 |
| WO | WO 2009/095429 A1 | 8/2009 |
| WO | WO 2009/095617 A2 | 8/2009 |
| WO | WO 2009/095618 A2 | 8/2009 |
| WO | WO 2009/095622 A1 | 8/2009 |
| WO | WO 2009/121853 | 10/2009 |
| WO | WO2009/121853 A1 | 10/2009 |
| WO | WO 2009/150385 A2 | 12/2009 |
| WO | WO 2010/010282 A1 | 1/2010 |
| WO | WO 2010/029039 | 3/2010 |
| WO | WO 2010/029039 A1 | 3/2010 |
| WO | WO 2010/029153 | 3/2010 |
| WO | WO 2010/029153 A1 | 3/2010 |
| WO | WO 2010/043813 A1 | 4/2010 |
| WO | WO 2010/066660 | 6/2010 |
| WO | WO 2010/136725 A1 | 12/2010 |
| WO | WO 2011054762 A2 | 5/2011 |
| WO | WO 2011054770 A1 | 5/2011 |
| WO | WO 2012025468 A1 | 1/2012 |
| WO | WO 2012016872 A1 | 2/2012 |
| WO | WO 2012/056005 A1 | 5/2012 |
| WO | WO 2013092338 A1 | 6/2013 |

OTHER PUBLICATIONS

Kleiboehmer W., et al, Solvay Werk Rheinberg: Integrierte Prozesse Separierte Abwasserbehandlungen—Gewaesserschultz, Wasser, Abwasser 200 (Wissenschaftlich-technische Mitteilungen des Instituts Zur Foerderung der Wasserguerte- und Wassermengenwirtschaft e; V;—2005 p. 81/-8/5., vol. 5.

Klaus Weissermel, et al., "Industrial Organic Chemistry," ($3^{rd}$ Completely Revised Edition); VCH 1997. p. 93-98.

Klaus Weissermel, et al., "Industrial Organic Chemisry," ($3^{rd}$ Completely Revised Edition); VCH 1997. p. 276-277.

Klaus Weissermel, et al., "Industrial Organic Chemistr," ($3^{rd}$ Completely Revised Edition); VCH 1997. p. 347-355.

Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).

Ying Ling Liu, "Phosphorous-Containing Epoxy Resins from a Novel Synthesis Route," Journal of Applied Polymer Science, vol. 83, 1697-1701 (2002).

J.B. Conant, et al, "Glycerol a,y-dichlorohydrin", Organic Syntheses Coll., 1941, vol. 1 p. 292-294 (5 pp.).

Gilman H., Organic Synthesis. Section 1, pp. 234-235 (no date)—attached English translation only.

Industrial Chemical Encyclopedia 5, p. 457 (no date)—attached English Translation only.

"Epoxy resins", p. 36-46, by Shanghai Resin Plane, Shanghai People's Press, 1971—attached English translation only.

Martinetti, R. et al., "Environment Le Recyclage du l'eau" Industrie Textile, Ste Sippe Sarl, Metz, FR, No. 1300 (Jul. 1, 1998), ISSN: 0019-9176 (no English abstract available)—8 pp.

"Rainwater Harvesting and Utilization" (United Nations Environment Program) Mar. 2002; XP003003726; Internet Citation extracted online on Jan. 1, 2006: URL:http://www.unep.or.ip/letc/Publication—4 pp.

Myszkowski, J. et al. "Removal of chlorinated organic impurities from hydrogen chloride"; English Chemical Abstract summary only of Polish Patent No. 136598 B2 (Mar. 31, 1986); XO002352444; 1 pp.

Myszkowski, J. et al. "Removal of organic compounds from gaseous hydrogen chloride by an absorption method" Chemia Stosowana (1986) vol. 30(4) p. 545-51; English Chemical Abstract Summary only; XP00235445; 1 pp.

Milchert, E. et al. "Recovering hydrogen chloride and organic compounds from the reaction mixture in the chlorination of ethylene"; English Chemical Abstract Summary only of Polish Patent No. 162910 B1 (Jan. 31, 1994); XP002352443; 1 pp.

RD 436093, Aug. 10, 2000, Akzo Nobel.

Ullmann's Encyclopedia of Industrial Chemistry, 2005, "pH Measurement and Control", Wiley-VCH GmbH & Co. KGaA, Weinheim, 10, 1002/14356007.e19_e01; pp. 1-31 (32 pgs).

U.S. Appl No. 14/366,278, Fouchet, filed Jun. 18, 2014.

Gielen, F.—Industrial Bioprocessing (2006) vol. 38, No. 3, pp. 8-9, Feb. 24, 2006 (2 pages).

Helmuth, G. et al.—Ullman's Encyclopedia of Insudtrial Chemistry (2005) Wiley-VCH Verlag GmbH & Co. KGaA. Weinheim, 10,1002/14356007.e19-e01, pp. 384-391 and pp. 400-403 (30 pages).

Siebert, O.W & Stoecker J.G.—Section 28: "Materials of Construction" in *Perry's Chemical Engineers Handbook*, 1997, $7^{th}$ Edition: pp. 28-1 to 28-64; Edited by: Perry, R.H.; Green, D.W., McGraw-Hill, 66 pgs.

(56) References Cited

OTHER PUBLICATIONS

Krisher, A.S. & Siebert, O.W.—Section 23: "Materials of Construction" in *Perry's Chemical Engineers Handbook*, 1984, 6th Edition: pp. 23-1, 23-2, 23-16, 23-17, 23-26 and 23-38; Edited by: Perry, R.H.; Green, D.W., McGraw-Hill, 8 pgs.
[Unknown Author] "Corrosion Resistance of Tantalum and Niobium Metals", 1998, Astrocosmos Metallurgical, Inc., pp. 2 to 6 & pp. 12 to 16 ; 10 pgs.
[Unknown Author]—"Teflon® PTFE fluoropolymer resin", Dupont Properties Handbook Brochure; Jul. 1996, 3 pgs.
Speight. J.,—"Halogenation", 2002, *Chemical Process and Design Handbook*, McGraw-Hill, pp. 1.21-1.23; 6 pgs.
Bartholome, E., et al., "Fungizide bis Holzwerkstoffe" Band 12. in *Ullmann's Encyklopädie der Technischen Chemie*, A3, 1976, Verlag Chemie, Weinheim, New York; pp. 367-375, 13 pgs—No English translation of text available.
Schroeder, K.—"Glycerine" 2008, in *Bailey's Industrial Oil and Fat Products*, 6th Edition, Edited by Fereidoon Shahidi; John Wiley & Sons, pp. 191-222; 32 pgs.
Thier, B. —3. Physikatlische und chemische Eigenschaften in *Apparate Technik—Bau-Anwendung*, 2, Ausgabe, Editors: Vulkan Verlag Essen 1997: pp. 203-211; 10 pgs—No English translation of text available.
Werthmuller, E.—"Auswahlkritieren fur Aiskleidungen mit Flurkunstoffen", *Chemie Technik* 1991, vol. 20, Issue 4, pp. 21-29, 5 pgs—Abstract in English—No English translation of text available.
U.S. Appl. No. 60/734,659, filed Nov. 8, 2005.
U.S. Appl. No. 60/734,627, filed Nov. 8, 2005.
U.S. Appl. No. 60/734,657, filed Nov. 8, 2005.
U.S. Appl. No. 60/734,658, filed Nov. 8, 2005.
U.S. Appl. No. 60/734,635, filed Nov. 8, 2005.
U.S. Appl. NO. 60/734,634, filed Nov. 8, 2005.
U.S. Appl. No. 60/734,637, filed Nov. 8, 2005.
U.S. Appl. No. 60/734,636, filed Nov. 8, 2005.
U.S. Appl. No. 60/560,676, filed Apr. 8, 2004, Gilbeau, et al.
U.S. Appl. No. 61/013,680, filed Dec. 14, 2007, Krafft, et al.
U.S. Appl. No. 61/013,713, filed Dec. 14, 2007, Gilbeau, et al.
U.S. Appl. No. 61/013,713, filed Dec. 14, 2007, Gilbeau.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,710, filed Dec. 14, 2007, Krafft, et al.
U.S. Appl. No. 61/007,661, filed Dec. 14, 2007, Boulos, et al.
Herman A. Bruson, et al., "Thermal Decomposition of Glyceryl Carbonates," Journal of the American Chemical Society, vol. 74, Apr. 1952 pp. 2100-2101.
Chemicals Guide, Chemical Daily Co., Ltd. (Published on Jun. 15, 1990) with attached English translation of relevant excerpts.
Perry's Chemical Engineers Handbook 7th Ed., 13th Section, 1997, pp. 13.1-13.108.
Perry's Chemical Engineers Handbook 7th Ed., 15th Section, 1997, pp. 15.1-15.47.
Ullmann's Encyclopedia of Industrial Chemistry 5th Ed., vol. A23, 1993, pp. 635-636.
Ullmann's Encyclopedia of Industrial Chemistry 5th Ed., vol. A13, 1989, p. 289.
Ullmann's Encyclopedia of Industrial Chemistry 5th Ed., vol. A11, 1986, pp. 354-360.
Application No. FR 06.05325 filed Jun. 14, 2006 by Solvay S.A.—priority document to EP2007/55742 published as WO 2007/144335 (attached herein) 17 pgs.
Application No. FR 07.53863 filed Mar. 15, 2007 by Solvay S.A and published as FR2913683, 19 pgs (attached herein)—priority document to EP2007/55742 published as WO2007/144335 29 pgs (attached herein).
Gibson, "The preparation, properties, and uses of glycerol derivatives, Part III. The Chlorohydrins", 1931, Chemistry and Industry, Chemical Society, pp. 949-975.
Carre et al, 1931, "La transformation des alcools polyatomiques en mono-et en polychlorohydrines au moyen du chlorure de thionyle",
Bulletin de la Societe Chimique de France, Societe Francaise de Chimie. Paris—ISSN 0037-8968, vol. 49, No. 49, pp. 1150-1154.
Fauconner, 1888, "Preparation de l'epichlorhydrine", Bull. Soc. Chim. FR, No. 50, pp. 212-214 (with enclosed translation in English).
Ullmann's Encyclopedia of Industrial Chemistry, "Industrially important epoxides", 1987, Fifth Completely Revised Edition, vol. A9, pp. 539-540.
Bonner et al, "The composition of constant boiling hydrochloric acid at pressures of 50 to 1220 millimeters", 1930, Journal of American Chemical Society, vol. 52, pp. 633-635.
Muskof et al, "Epoxy Resins" in Ullmann's Encyclopedia of Industrial Chemistry, 1987, 5th Ed., vol. A9, pp. 547-563.
Novelli, A., "The preparation of mono-and dichlorohydrins of glycerol", 1930, Anales Farmacia Bioquimica, vol. 1, pp. 8-19 (with English abstract).
Derwent Publications, AN 109:6092 CA, JP 62-242638, Oct. 23, 1987, 1 pg.
Derwent Publications, AN 1987-338139 [48], JP 62-242638, Oct. 23, 1987, 1 pg.
I. Miyakawa et al, Nagoya Sangyo Kagaku Kenkyusho Kenkyu Hokoku, 10, 49-52 (1957). (Abstract in English only). 1 pg.
Han Xiu-Ying et al, Shanxi Daxue Xuebao Bianjibu, 2002, 25(4), 379-80. (Abstract in English only), 1 pg.
Semendyaeva et al, 1981. Kimicheskaya Promyshlennost, Seriya: Khomaya Promyshlennost, 5. 21-2 (CA Summary). XP 002465275, 1 pg.
Rudnenko, EV, et al., 1988, Lakokrasochnye Materially i 1kh Primenenie, 4 69-71 (CA Summary) XP 002465276, 1 pg.
Kirk-Othmer Encyclopedia of Chemical Technology, 1978, 3rd Ed., vol. 4, Blood, Coagulants and Anticoagulants to Cardiovascular Agents. p. 847-848.
Jeffrey Lutje Spelberg, et al, A Tandem Enzyme Reaction to Produce Optically Active Halohydrins, Epoxides and Dials, Tetrahedron: Asymmetry, Elsevier Science Publishers, vol. 10, No. 15, 1999, pp. 2863-2870.
Oleoline.com. Glycerine Market Report. Sep. 10, 2003, No. 62, 31 pgs.
Notification Under Act. No. 100/2001, Coll. As Amended by Act. No. 93/2004, Coll. To the extent of Annex No. 4, (SPOLEK) Nov. 30, 2004, 80 pgs.
Documentation Under Act. No. 100/2001 Coll. As Amended by Act. No. 93/2004 Coll in the scope of appendix No. 4 (SPOLEK) Jan. 11, 2005, 86 pgs.
K. Weissermel & H.J. Arpe. Industrial Organic Chemistry, Third, Completely Revised Edition, VCH, 1997, pp. 149 & 275.
Industrial Bioproducts: "Today and Tomorrow." Energetics, Inc. for the U.S. Department of Energy, Office of Energy Efficiency and Renewable Energy, Office of the Biomass Program, Jul. 2003, pp. 49, 52 to 56.
Kirk Olhmer Encyclopedia of Chemical Technology, Fourth Edition, 1992, vol. 2, p. 156, John Wiley & Sons, Inc.
Ullmann's Encyclopedia of Industrial Chemistry, Fifth, Completely Revised Edition, 1988, vol. A13, pp. 292-293.
The Merck Index, Eleventh Edition, 1989, pp. 759-760.
Ullmann's Encyclopedia of Industrial Chemistry, Fifth completely Revised Edition, vol. A1, 1985, pp. 427-429.
Ullmann's Encyclopedia of Industrial Chemistry, Fifth Completely Revised Edition, vol. A6, 1986, pp. 240-252.
Hancock, E.G., Propylene and its Industrial Derivatives, 1973, pp. 298-332.
K. Weissermel & H.J. Arpe, Industrial Organic Chemistry, Third, Completely Revised Edition, VCH 1997, pp. 275-276.
K. Weissermel & H.J. Arpe, in Industrial Organic Chemistry, Third, Completely Revised Edition, VCH 1997, pp. 275-276.
Robert T. Morrison & Robert N. Boyd, Organic Chemistry, 5th Ed., vol. II, pp. 666-667 and 712 to 714 (Japanese Translation), published on Jul. 10, 1970, Tokyo Kegeku Dozin Co., Ltd. (and similar passages but retrieved from the English Fifth Edition of the Book. 1987).
Perry's Chemical Engineers' Handbook, Sixth Edition, Robert H. Perry, Don Green, 1984, Section 21-64 to 21-68.
Iwanami et al, Dictionary of Physics and Chemistry, Third Edition, Ryo Midorikawa /Iwanami Shoten, Publishers, May 29, 1971, pp. 270-271, 595 and 726.

(56) References Cited

OTHER PUBLICATIONS

Expert Opinion on the Environment Impact Assessment Documentation Pursuant to Annex No. 5 of Act No. 100/2001 Coll., as amended by later regulations of the project/intent combined process for the manufacture of epichlorohydrin (SPOLEK) Apr. 2005.
Kirk Othmer Encyclopedia of Chemical Technology, Third Edition, vol. 12, 1980, pp. 1002-1005.
Chemical Engineering Handbook, the 6th Edition, Edited by the Society of Chemical Engineers, published by Maruzen Co, Ltd. 1999, pp. 1296-1306 Pub. Feb. 25, 1999 w/English translation of p. 1296, Table 28.4, p. 1298, left column, lines 4-13 and p. 1305, Table 28.10.
Product Brochure of De Dietrich Company, Apr. 1996, pp. 3, 8 and 9 w/English translation of p. 8, left column, lines 1-4, p. 9.
The Journal of the American Chemical Society, vol. XLV, Jul.-Dec. 1923, pp. 2771-2772.
Berichte Der Deutschen Chemischen Gesellschaft, 1891, vol. 24, pp. 508-510.
Catalogue of Nittetu Chemical Engineering Ltd. (Published on Mar. 1944).
12093 Chemicals, The Chemical Daily Co., Ltd. (Published on Jan. 22, 1993) with attached English translation of relevant excerpts, 24 pgs.
Ma Zengxin et al, "recovery of Polyglycerol from residues of Synthetic Glycerol" Riyong Huaxue Gongye, 1997, 4, 21023 (English Abstract only).
Sang Hee Lee et al "Direct preparation of Dichloropropanol (DCP) from Glycerol Using Heteropolyacid (HPA) Catalysts: A Catalyst Screen Study," Catalysis Communications (9), 2008, p. 1920-1923.
Production and Prospect of the World Natural Glycerol by Zhu Shiyong, Cereals and Oils, vol. 1, 1997, pp. 33-38 (No English Translation).
Vinnolit; Vinnolit received EU grant for water recycling project: Press Release. 2008. http://www.vinnolit.de/vinnolit.nst/id/EN_Vinnolit_receives_EU_grant_for_water_recycling_project.
N.W Ziets, Journal of American Oil Chemists' Society, Nov. 1956, vol. 33, pp. 556-565.
Perry's Chemical Engineers Handbook, Sixth Edition, McGraw Hill Inc., (1984) Section 18.
Vol. 83: Unit Operations II of Ulmann's Encyclopedia of Industrial Chemistry, Fifth Completely Revised Edition, Published by VCH, 1988.
W. Geiger et al, "14C/12C-Ratios in Organic Matter and Hydrocarbons Extracted from Dated Lake Sediments", Nuclear Instruments and Methods in Physics Research B5 (1984), pp. 394-397, XP-002631954.
Jurgen O. Metzger, "Fats and Oils as Renewable Feedstock for Chemistry," Eur. J. Lipid Sci. Technol. (2009), vol. 11, pp. 865-876, XP-002631953.
Bruce M. Bell, "Glycerin as a Renewable Feedstock for Epichlorohydrin Production. The GTE Process", Clean-Soil, Air, Water, (1008) vol. 36, No. 8, pp. 657-661, XP-002631952.
Horsley, Lee H.—"Azeotropic Data-III", The Dow Chemical Co., Midland, MI, American Chemical Society 1973, pp. 1-4; 4 pgs.
Suzawa, Yoshikazu, et al—"Incineration System for Waste Liquid Containing Chlorinated Oragnic Compounds", Chemical Apparatuses, 1981, vol. 23, No. 11, 34 pgs, Translation in English provided.
D'Alonzo, R.P., et al—"Glyceride Composition of Processed Fats and Oils As Determined by Glass Capillary Gas Chromatography", Journal of American Oil Chemists' Society, 1982, vol. 59, No. 7, pp. 292-295; 4 pgs.
Chemical Engineering Handbook, $6^{th}$ Revised Edition, 2001, pp. 1-36; 56 pgs; Translation in English provided.
"Electrolytic cell test electrolysis of epoxy sewage salt to prepare chlor-alkali", Process Equipment Department of Research Institute of Chloro-Alkali, Shengyang Chemical Plant, Liaoning Chemical Industry, Issue No. 2, pp. 32-37, published Dec. 31, 1981; 17 pgs; Translation in English provided.
Chengxin, Ren, et al—"Analysis on the Composition of the By product During the Manufacturing Process of S-Epichlorohydrin by GC-MS", Chemical Analysis and Meterage, 2003, vol. 12, Issue No. 3, pp. 25-26; 6 pgs; Translation in English provided.
Encyclopedia of Chemical Technology, vol. 5, Nov. 1993; 6 pgs; Translation in English provided.
"Manufacture and use of epoxy resin", edited by Shanghai Resin Factory, published by China Petrochemical Press, First Edition, Oct. 1974; 16 pgs; Translation in Eglish provided.
Gilma, Henry, et al—"Organic synthesis", Part 1, published by Scientific Publishing, 1957 (with abstract); 4 pgs.
Handbook of Chemical Products, Heavy Organic Chemicals, Second edition, published by Chemical Industry Press, Jan. 1995; 13 pgs; Translation in English provided.
Kiseleva, R. A., et al—"Study of the Interaction Dibasic Acids with Glycerol", J. App. Chem. USSR, 1971, vol. 44, pp. 2086-2090; 5 pgs.
Handbook of Corrosion Data and Material Selection, published by Chemical Industry Press, edited by Jingyi Zuo, Yu Zuo; First edition, Oct. 1995, 5 pgs; Translation in English provided.
Handbook of Azeotropic Mixture, edited by Information Department of Comprehensive Scientific Technology Research Institution of Fushun City, 1993; 8 pgs; Translation in English provided.
"Industry Chemical Reaction and Application", published by Chinese Scientific Technology University Press, 1999; 4 pgs; Translation in English provided.
"Epoxy resin", published by Shanghai People's Publishing House, 1971; Translation in English provided; 21 pgs.
Boschan, Robert, et al—"The Role of Neighboring Groups in Replacement Reactions. XXI. Front-side Participation of Acetoxy Group. Catalytic Effect of Acetic Acid on the Reaction of Glycols with Hydrogen Chloride", Journal of the Americal Chemical Society, 1956, vol. 78, pp. 4921-4925; 5 pgs.
Encyclopedia for Chinese Adult Education, 1994, p. 623; 10 pgs; Translation in English Provided.
[Unknown Author]—New Experimental Chemical Course 1, Basic Operation I. Section 4, Separation and Purification, pp. 251-252 (issued on Sep. 20, 1975) with English translation from Shiga Interantional Patent Office, 3 pgs.
March, Jerry—"Reactions, Mechanisms & Structure", Advanced Organic Chemistry, $4^{th}$ Ed., 1992, pp. 889, 908 and 937; 5 pgs.
[Unknow Author]—Bulletin de la Société Chimique de Paris—"Analyse des Travaux de Chimie Pure et Appliquée". G. Masson, Editor, Paris, Jul. 4, 1873, Novelle Série, Tome XIX. pp. 97-99; 4 pgs; comments regarding Friedel & Silva's work on middle of p. 98.
Neuberg, Irene Stephanie—"A New Way of Preparing Glyceraldehyde from Glycerol", Kaiser Wilhelm Institute in Berlin for Biochemi-Dahlem. 1930; 3 pgs; Includes abstract in English.
Krauz, Francois—'Recherches sur les Aldehydes Substitues en α en β, α and β Substituted Aldehydes', University Strasbourg, France ; Ann Chim 12, Nov.-Dec. 1949, 4, pp. 811-831, 23 pgs ; Includes abstract in English.
[Unknow Author]—"Glycerine—An Overview"—by The Soap and Detergent Association, Glycerine and Oleochemical Division, 1990; 27 pgs.
[Unknown Author]—"Commerical Synthesis of Glycerol Begins a New Shell Chemical Corp Plant—A Staff Report"; Chemical & Engineering News, 1948, vol. 26, No. 38, pp. 2770-2771; 2 pgs.
Fairborne, Arthur, et al—"The Partial Esterification of Polyhydric Alcohols. Part XII. The Funstion of Ethylene-oxide Rings", J. Chem. Soc. 1932, republished 1965, , pp. 1965-1972; 8 pgs.
Clarke, H.T., et al—"Epichlorohydrin", Organic Syntheses, Coll. vol. 1, pp. 233 (1941); vol. 3, p. 47 (1923); 2 pgs.
Braun, Geza—"Epichlorohydrin and Epibromohydrin", Organic Sythneses, Coll. vol. 2, p. 256 (1943); vol. 16, p. 30 (1936); 2 pgs.
Conant, J.B., et al—"Glycerol a,y-Dichlorohydrin", Organic Syntheses, Coll. vol. 1, p. 292 (1941); vol. 2. p. 29 (1922); 3 pgs.
Chavanne, G.—"Memoires presentes a la Societe Chimique", English translation—"Reports Submitted to Chemical Firm", Bull. Soc. Chim. Fr. 1943, 1, EP 06 121 086; 16 pgs.
Schroder, Angela, et al—"Glycerol as a by-product of biodiesel production in Diets for ruminants", 1999, The Regional Institute, Institute of Animal Nutrition, Physiology and Metabolism, University of Kiel, Germany, 6 pgs.
[Unknown Author]—"Chemical Properties and Derivatives of Glycerol", 1965, Glycerine Producer's Association, $1^{st}$ Edition, 23 pgs.

(56) References Cited

OTHER PUBLICATIONS

Busby, G.W., et al—"The Purification of Glycerin by Ion-Exchange", The Journal of the American Oil Chemists' Society, 1952, 3 pgs.
Lamborn, Leebert Lloyd—"Modern Soaps, Candles and Glycerin", 3rd Edition, 1918, D. Van Nonstrand Company, London, 12 pgs.
Knothe, Gerhard—"Historical perspectives on vegetable oil-based diesel fuels", Industrial Oils, 2001, vol. 12, pp. 1103-1107; 5 pgs.
Schuchardt, Ulf, et al—"Transesterification of Vegetable Oils: A Review", 1998, Braz. Chem Soc., vol. 9, No. 1, pp. 199-210; 12 pgs.
Claude, Sylvain—"Research of new outlets of glycerol—recent developements in France"—1999, Fett/Lipid, No. 3, Wiley-VCH Verlag GmbH, Weinheim, pp. 101-104; 4 pgs.
Prakash, Chandra B.—"A Critical Review of Biodiesel as a Transportation Fuel in Canada", 1998, GCSI—Global Change Strategies International Inc.; 119 pgs.
Fukuda, Hideko, et al—"Review—Biodiesel Fuel Production by Transesterification of Oils", 2001, Journal of Bioscience and Bioengineering; vol. 92, No. 5, pp. 405-416; 12 pgs.
Yong, K.C. et al—"Refining of Crude Glycerine Recovered From Glycerol Residue By Simple Vacuum Distillation", Dec. 2001, Journal of Oil Palm Research, vol. 13, No. 2, pp. 39-44, 6 pgs.
Clarke, H.T., et al—"Epichlorohydrin", "Ethyl Acetoacetate", 1964, Organic Syntheses, Collective vol. 1, Being a Revised Edition of Annual vol. I-IX, Second Edition, Tenth Printing, John Wiley & Sons, Inc.; pp. 232-235; 6 pgs.
Braun, Geza—"Epichlorohydrin and Epibromohydrin", 1957, Organic Syntheses, Inc., Collective vol. 2. A Revised Edition on Annual vols. X-XIX. Eighth printing, John Wiley & Sons, Inc., pp. 256-258: 5 pgs.
Kirk-Othmer, Encyclopedia of Chemical Technology, Third Edition, vol. 9, Herman F. Mark, et al, Editors—"Epoxy Resins", 1980, pp. 267-290, A Wiley-Interscience Publication, John Wiley & Sons, Inc.: 28 pgs.
Encyclopedia of Experimental Chemistry I. Basic Operation I, edited by The Chemical Society of Japan Nov. 5, 1990, 4th Edition, pp. 161-165 and pp. 184-191, Maruzen Co., Ltd.; 16 pgs.
Encyclopedia of Chemistry 3, edited by Editorial Committee of Encyclopedia of Chemistry, Kyoritsu Shuppan Co., Ltd., Sep. 30, 1960. 1st Edition. 1st printing, pp. 312-313; 2 pgs.
Wu, Guoyung, et al—"Preparation of Biodiesel and Glycerol by Methyl Esterification of Cottonseed Oil", 2003, China Oil and Fat, vol. 28, Issue No. 4, pp. 70-73; 15 pgs, in Chinese, Translation provided in English.
Zhu, Shiyong—"Production and prospects of the world's natural glycerin", 1997, Cereals and Oils, Issue No. 01, pp. 33-38; 21pgs: in Chinese: Translation provided in English.
Hill, Arthur J., et al—"A Synthesis of Beta-Chloro-Allyl Chloride", 1922, Journal American Chemical Society, vol. 44, Issue No. 11, pp. 2582-2595; 15 pgs.
Physical and Chemical Dictionary (5th Edition), "Glass Lining"; "Porcelain Enamel", 1998; pp. 267, 378, 738, 1298 and 1403; 8 pgs; in Japanese, Partial translations provided in English for pp. 267 and 1298.
Encyclopedia Chimica, No. 8, (1st Edition), "Enamel. porcelain enamel. vitreous enamel": 1962: 4 pgs: in Japanese; Partial translation provided in English.
Encyclopedia Chimica. No. 2, (1st Edition). "Glass lining", 1960; 4 pgs; in Japanese; Partial translation provided in English.
Gottlieb, Klaus, et al—"Glycerine—a sustainable raw material", 1994, Chem. Ing. Tech., vol. 66, Issue No. 1. pp. 64-66: 8 pgs; in German; Translation provided in English.
Wessendorf, Richard—"Glycerinderivate als Kraftstoffkomponenten", 1995, Wissenschaft & Technik, Science and Technology, pp. 138-143: 6 pgs; in German; no English translation provided.
Milchert, E , et al—"Dehydrochlorination of Glycerol Dichlorohydrin to Epichlorohydrin", 1995, Chem. Papers, vol. 49, Issue No. 3, pp. 133-136, 4 pgs.

Trent, D., et al—"Reactive stripping in a rotatin packed bed for the production of hypochlorous acid", 1999, BHR Group Conference Series Publication. vol. 38 (Process Intensification for the Chemical Industry), pp. 217-231: 15 pgs.
Vajda, M., et al—"Membrane-Based Extraction Joined with Membrane-Based Stripping in a Circulating Arrangement II. Extraction of Organic Acids", 2003, Chemical Papers, vol. 57, Issue No. 1, pp. 3-10; 9 pgs.
Demarquay, M.—"De la Glycerine de ses Applications a la Chirurgie et a la Medecine", 1863, Librairie de la Faculte de Medecine, Paris, France; 26 pgs; no English translation provided. Best copy available.
Perry's Chemical Engineers' Handbook, Sixth Edition—"Process Control, Temperature Measurements", 1984, McGraw Hill Inc., Section 22, pp. 22-32-22-37; 8 pgs; Best copy available.
Perry's Chemical Engineers' Handbook, Sixth Edition—"Mass Transfer and Gas Absorption", 1984, McGraw Hill Inc., Section 14, pp. 14-1-14-40; 42 pgs; Best copy available.
U.S. Appl. No. 13/813,348, filed Jan. 30, 2013, Patrick Gilbeau, et al.
U.S. Appl. No. 13/818,753, filed Feb. 25, 2013, Patrick Gilbeau, et al.
Kaszonyi, A., et al—"Bioglycerol a new platform chemical", 2009, 44th International Petroleum Conference, Bratislava, Slovak Republic; pp. 1-8; 8 pgs.
Williamson, R., et al—"DE-FC36-03GO13000 Final Report: Continuous Isosorbide Production from Sorbitol using Solid Acid Catalysis", 2006, DOE Award for Iowa Corn Promotion Board: 9 pgs.
Malhotra, S. V., et al—"Applications of Corn-Based Chemistry", 2007, The Bridge Publication of the National Academy of Engineering, 2007, vol. 34, Issue No. 4; 8 pgs; Best copy available.
Jaffe, M., et al—"Corn(Sugars) Based Chemistries for the Polymer Industry", 2009, ANTEC, 67th Annual Technical Conf., Proceeded., Society of Plastic Engineers, Jun. 22-24, Mc Cormick Place West Chicago, IL, 6 pgs.
[Unknown Author]—"Iowa Corn Promotion Board, NJIT to License Breakthrough, Safe Bio-Plastic Alternative", Aug. 6, 2008, New Jersey Science & Technology University Press Release; 2 pgs.
[Unknown Author]—"NJIT Patent May Be Able To Replace BPA; Make Consumer Products Safer", Feb. 4, 2010, New Jersey Science & Technology University Press Release; 2 pgs.
Fenouillot, F., et al—"Polymers from renewable 1,4:3,6-dianhydrohexitols (isosorbide isomannide and isoidide): A Review", 2010, Progress in Polymer Science, vol. 35, Issue No. 5, pp. 578-622; 45 pgs.
[Unknown Author], Kirk Othmer Encyclopedia of Chemical Technology—vol. 2, p. 156, John Wiley and Sons, 1992.
J.B. Conant, et al, "Glycerol, a,y-dichlorohydrin", Organic Syntheses Coll., 1941, vol. 1, p. 292-294 (5 pp.).
Gilman H., Organic Synthesis. Section 1, pp. 234-235 (no date)—attached English translation only, 1922.
Industrial Chemical Encyclopedia 5, p. 457 (no date)—attached English translation only, 1966.
"Epoxy resins", p. 36-46, by Shangai Resin Plant, Shanghai People's Press, 1971—attached English translation only.
Martinetti, R. et al. "Environment Le Recyclage du l'eau" Industrie Textile. Ste Sippe Sarl, Metz, FR, No. 1300 (Jul. 1, 1998), ISSN:0019-9176 (no English abstract available)—8 pp.
"Rainwater Harvesting and Utilization" (United Nations Environment Program) Mar. 2002: XP003003726; Internet Citation extracted online on Jan. 1, 2006: URL:http://www.unep.or.ip/letc/Publication—4 pp.
Myszkowski, J. et al. "Removal of chlorinated organic impurities from hydrogen chloride", English Chemical Abstract summary only of Polish Patent No. 136598 B2 (Mar. 31, 1986), XP002352444; 1 pp.
Myszkowski, J. et al. "Removal of organic compounds from gaseous hydrogen chloride by an absorption method" Chemia Stosowana (1986) vol. 30(4) p. 545-51; English Chemical Abstract Summary only; XP002352445; 1 pp.
Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.
Laine, D.F. et al. "The destruction of organic pollutants under mild reaction conditions; A review" Michochemical Journal, vol. 85, No. 2, 2007 pp. 183-193; available online Aug. 17, 2006; 12 pp.

\* cited by examiner

DERIVATIVE OF EPICHLOROHYDRIN OF NATURAL ORIGIN

REFERENCE TO RELATED APPLICATIONS

This application is a U.S. national stage entry under 35 U.S.C. §371 of International Application No. PCT/EP2011/066689 filed Sep. 26, 2011, which claims priority to European patent application no 10183593.2 filed on Sep. 30, 2010, the whole content of this application being incorporated herein by reference for all purposes.

Should the disclosure of any of the patents, patent applications, and publications which are incorporated herein by reference conflict with the description of the present application to the extent that it may render a term unclear, the present description shall take precedence.

TECHNICAL FIELD OF THE INVENTION

The present invention relates to a derivative of epichlorohydrin, to the use of epichlorohydrin for manufacturing such derivative, to a process for manufacturing such a derivative and to the use of such a derivative. The present invention relates more specifically to a derivative of epichlorohydrin of natural origin, to the use of epichlorohydrin of natural origin for manufacturing such a derivative, to a process for manufacturing such a derivative and to the use of such a derivative.

BACKGROUND OF THE INVENTION

Epoxy resins are an important class of derivatives of epichlorohydrin. Nowadays, almost 90% of the world production of epoxy resins is based on the reaction between Bisphenol A (2,2-bis(4'-hydroxyphenyl)propane) and epichlorohydrin. Health issues have recently been raised linked to the estrogenic properties of Bisphenol A which might be released in epoxy resins derived articles due to polymer decay with time.

International application WO 2008/147473 discloses a process for the preparation of isosorbide diglycidyl ether as substitute to Bisphenol A diglycidyl ether (DGEBA), by reacting isosorbide with epichlorohydrin. Such a compound and derived products may however contain impurities which may render them unsuitable for certain applications. Those impurities can remain in the final products and possibly degrade with a concomitant deterioration of the properties of the final products. They can exhibit or degrade in compounds exhibiting some toxicity leading to safety issues especially when the final products are intended to be in contact with food and drink. Moreover, they can accumulate in and contaminate industrial process waters such as wastewaters for instance.

The goal of the present invention is to solve those problems by providing a new derivative of epichlorohydrin suitable in all known applications.

DESCRIPTION OF THE INVENTION

The invention therefore relates in a first embodiment to a derivative of epichlorohydrin of natural origin, selected from the group consisting of glycidyl ethers presenting an epoxide equivalent weight higher than or equal to 50 g/equivalent and lower than or equal to 15000 g/equivalent, of glycidyl esters, of glycidyl amides, of glycidyl imides, of glycidyl amines, and any mixture thereof, and of which the $^{14}C$ mass content is such that the ratio $^{14}C/^{12}C$ is higher than $0.70 \times 10^{-12}$. One of the essential characteristics of the present invention resides in the $^{14}C/^{12}C$ ratio. When such a ratio is obtained, the amount of detrimental impurities can be lowered in the derivative, in the streams of the process for making the derivative and in the final articles that can be obtained from such derivatives.

By epichlorohydrin of natural origin, one intends to denote an epichlorohydrin of which at least 10% has been obtained from renewable raw materials, preferably of which at least 50% has been obtained from renewable raw materials, more preferably of which at least 75% has been obtained from renewable raw materials, still more preferably of which at least 90% has been obtained from renewable raw materials, yet more preferably of which at least 95% has been obtained from renewable raw materials, and most preferably at least 99% has been obtained from renewable raw materials. An epichlorohydrin of which at most 99.99% has been obtained from renewable raw materials is also suitable. An epichlorohydrin which has been obtained only from renewable raw materials is particularly convenient.

By epichlorohydrin obtained from renewable raw materials one intends to denote an epichlorohydrin of which at least part of the carbon backbone, preferably all the carbon backbone, originates from renewable raw materials, whatever the process and the starting materials used for manufacturing such an epichlorohydrin.

The derivative of epichlorohydrin of natural origin according to the invention is selected from the group consisting of glycidyl ethers presenting an epoxide equivalent weight higher than or equal to 50 g/equivalent and lower than or equal to 15000 g/equivalent, of glycidyl esters, of glycidyl amides, of glycidyl imides, of glycidyl amines, and of any mixture thereof.

The derivative of epichlorohydrin of natural origin can be selected from the group consisting of, a glycidyl ester, a glycidyl ether, a glycidyl amide, a glycidyl amine, a glycidyl imide, any mixture thereof and any combination thereof. The glycidyl ester can be a monoester or a polyester, often a diester. The glycidyl ester can be selected from the group consisting of a monomer, a polymer, and any mixture thereof. The glycidyl ester is preferably a monomer and more preferably a polymer. A glycidyl ester is frequently encountered. The glycidyl ether can be a monoether or a polyether, often a diether. The glycidyl ether can be selected from the group consisting of a monomer, a polymer, and any mixture thereof. The glycidyl ether is preferably a monomer and more preferably a polymer. A glycidyl ether is often encountered. The glycidyl amide can be a monoamide or a polyamide, often a diamide. The glycidyl amide can be selected from the group consisting of a monomer, a polymer, and any mixture thereof. The glycidyl amide is preferably a monomer and more preferably a polymer. A glycidyl amide is often encountered. The glycidyl amine can be a monoamine of a polyamine, preferably a diamine. The glycidyl amine can be selected from the group consisting of a monomer, a polymer, and any mixture thereof. The glycidyl amine is preferably a monomer and more preferably a polymer. A glycidyl amine is often encountered. The glycidyl imide can be a monoimide or a polyimide, often a dimide. The glycidyl imide can be selected from the group consisting of a monomer, a polymer, and any mixture thereof. The glycidyl imide is preferably a monomer and more preferably a polymer. A glycidyl imide is often encountered. The glycidyl imine can be a monoimine or a polyimine, often a diimine. The glycidyl imine can be selected from the group consisting of a monomer, a polymer, and any mixture thereof. The glycidyl imine is preferably a monomer and more preferably a polymer. A glycidyl imine is often encountered. The combination can be selected from the group consisting of a glycidyl ether-ester, a glycidyl amino-ester, a glycidyl amido-ether, a glycidyl imido-ether, or any mixture thereof.

The derivative of epichlorohydrin of natural origin according to the invention is preferably selected from the group consisting of glycidyl ethers presenting an epoxide equivalent weight higher than or equal to 50 g/equivalent and lower than or equal to 15000 g/equivalent.

The derivative of epichlorohydrin of natural origin according to the invention can be selected from the group consisting of a resin, a product that can be used as coagulant, a wet-strength resin, a cationization agent, a flame retardant, an ingredient for detergents, an elastomer and any mixture thereof.

The derivative of epichlorohydrin of natural origin according to the invention is preferably a polyglycidyl ether. The polyglycidyl ether can be selected from the group consisting of a monomer, a polymer, and any mixture thereof. The polyglycidyl ether is preferably a monomer and more preferably a polymer.

By polymer, one intends to denote molecules with many units joined to each other through chemical covalent bonds, often in a repeating manner, those units being referred as repeat units. The number of repeat units is higher than zero. A polymer contains at least one type of repeat units. When the polymer contains only one type of repeat units, it is called a homopolymer. When the polymer contains more than one type of repeat units, it is called a copolymer. The copolymers can be of the random type, of the alternating type or of the block type, such as described in "Polymer Science Dictionary, M.S.M., Elsevier Applied Science, London and New York 1989, page 86".

The polyglycidyl ether of the present invention is preferably a resin and more preferably an epoxy resin.

By epoxy resin, one intends to denote a polyglycidyl ether polymer, the chemical formula of which contains at least two 2,3-epoxypropyloxy groups.

The $^{14}C$ content of a product is an indication of the use of natural and renewable raw materials to manufacture the product. Indeed, contrary to fossil raw materials, all materials composed of renewable raw materials contain $^{14}C$. All carbon samples derived from living organisms (animals or plants) are made of a mixture of 3 isotopes: $^{12}C$ (representing ~98.892%), $^{13}C$ (~1.108%) and $^{14}C$ (traces: $1.2 \times 10^{-10}$%). The ratio $^{14}C/^{12}C$ of living tissues is identical to that of the atmosphere. In the environment, $^{14}C$ exists under two major forms: mineral that is to say carbon dioxide ($CO_2$) and organic, that is to say carbon integrated in organic molecules.

In a living organism, the ratio $^{14}C/^{12}C$ is kept constant by the metabolism because the carbon is continuously exchanged with the environment. The proportion of $^{14}C$ being roughly constant in the atmosphere, it is the same in the organism, when still living, because it absorbs that $^{14}C$ as it absorbs $^{12}C$. The average $^{14}C/^{12}C$ ratio is equal to $1.2 \times 10^{-12}$.

$^{12}C$ is stable that is to say that the number of $^{12}C$ in a given sample is constant with time. $^{14}C$ is radioactive and each gram of $^{14}C$ of living being contains enough $^{14}C$ to give 13.6 disintegrations per minute.

The half-life time (period) $T_{1/2}$, linked to the disintegration constant of $^{14}C$ is of 5730 years. Taking this duration into account, one can consider that the $^{14}C$ content is practically constant from the extraction of renewable raw materials (animal or plant origin) to the manufacture of the final product.

Today, there exist at least two different techniques for measuring the $^{14}C$ content of a sample:
  by liquid scintillation spectrometry
  by mass spectrometry: the sample is converted into graphite or gaseous $CO_2$, analyzed by mass spectrometry. This technique uses accelerator and a mass spectrometer to separate $^{14}C$ and $^{12}C$ ions and therefore to determine the ratio of the two isotopes.

All those methods for measuring the $^{14}C$ content of a sample are precisely described in standards ASTM D 6866 (notably D 6866-06 and D 6866-08) and in standards ASTM 7026 (notably D 7026-04). The method preferably used is the mass spectrometry described in standard ASTM D6866-08 ("accelerator mass spectroscopy").

In the derivative of epichlorohydrin of natural origin according to the invention, the $^{14}C$ mass content is such that the ratio $^{14}C/^{12}C$ is preferably higher than to or equal to $0.75 \times 10^{-12}$, more preferably higher than to or equal to $0.8 \times 10^{-12}$, still more preferably higher than to or equal to $0.9 \times 10^{-12}$, yet more preferably higher than to or equal to $1.0 \times 10^{-12}$, most preferably higher than or equal to $1.1 \times 10^{-12}$ and could reach a value equal $1.2 \times 10^{-12}$. In this last case, all the carbon elements used to manufacture the derivative of the invention will be of renewable (i.e. non fossil) natural origin.

A derivative of epichlorohydrin of natural origin according to the invention, of which the $^{14}C$ mass content is such that the ratio $^{14}C/^{12}C$ is equal to $1.2 \times 10^{-12}$ is convenient.

When the derivative of epichlorohydrin of natural origin is a glycidyl ether, specifically a polyglycidyl ether, more specifically when the polyglycidyl ether is a polymer and most preferably when the polyglycidyl ether is an epoxy resin, it can further exhibit at least one of the four following characteristics.

Its epoxide equivalent weight (EEW) expressed in g/equivalent is usually higher than or equal to 100, often higher than or equal to 150, frequently higher than or equal to 500, in many cases higher than or equal to 1000, and more specifically higher than or equal to 5000 and its epoxide equivalent weight is usually lower than or equal to 12000, often lower than or equal to 10000, frequently lower than or equal to 8000, in many cases lower than or equal to 7000, and more specifically lower than or equal to 6000. The epoxide equivalent weight is the weight of resin required to obtain 1 equivalent of epoxide functional group and it is obtained according to ASTM Standard D 1652.

Its epoxy value in equivalent per 100 g of derivative is generally higher than or equal to 0.008, usually higher than or equal to 0.009, often higher than or equal to 0.01, frequently higher than or equal to 0.013, in many cases higher than or equal to 0.014, and more specifically higher than or equal to 0.017 and its epoxy value is generally lower than or equal to 1.0, usually lower than or equal to 0.8, often lower than or equal to 0.7, frequently lower than or equal to 0.2 and in many cases lower than or equal to 0.1. The epoxy value in equivalent per 100 g is the number of epoxy groups per 100 g of resin and it is obtained according to ASTM Standard D 1652.

Its dynamic viscosity at 25° C. is generally higher than or equal to 50 mPa·s, usually higher than or equal to 100 mPa·s, often higher than or equal to 500 mPa·s, frequently higher than or equal to 1000 mPa·s, in many cases higher than or equal to 5000 mPa·s, and more specifically higher than or equal to 10000 mPa·s and its dynamic viscosity is generally lower than or equal to 50000 mPa·s, usually lower than or equal to 30000 mPa·s, often lower than or equal to 20000 mPa·s, frequently lower than or equal to 17000 mPa·s, in many cases lower than or equal to 15000 mPa·s, and more specifically lower than or equal to 10000 mPa·s. The viscosity at 25° C. is obtained according to ASTM Standard D 445.

Its content of hydrolysable chloride is generally higher than or equal to 0.01%, usually higher than or equal to 0.02%, often higher than or equal to 0.05%, frequently higher than or equal to 0.07%, in many cases higher than or equal to 0.1%, and more specifically higher than or equal to 0.15%, and its content of hydrolysable chloride is generally lower than or equal to 2.2%, usually lower than or equal to 1%, often lower than or equal to 0.8%, frequently lower than or equal to 0.6%, in many cases lower than or equal to 0.5%, and more specifically lower than or equal to 0.4%. The hydrolysable content is obtained according to ASTM Standard D 1726.

When the derivative of epichlorohydrin of natural origin is a glycidyl ether, specifically a polyglycidyl ether, more specifically when the polyglycidyl ether is a polymer and most preferably when the polyglycidyl ether is an epoxy resin, it can further exhibit at least one of the following characteristics wherein the glycidyl ether exhibits in addition at least one of the following characteristics:

an epoxy value in equivalent per 100 g of derivative higher than or equal to 0.008 and lower than or equal to 1.0,
a dynamic viscosity at 25° C. higher than or equal to 50 mPa·s and lower than or equal to 50000,
a content of hydrolysable chloride higher than or equal to 0.01% and lower than or equal to 2.2%.

When the derivative of epichlorohydrin of natural origin is a glycidyl ether, specifically a polyglycidyl ether, more specifically when the polyglycidyl ether is a polymer and most preferably when the polyglycidyl ether is an epoxy resin, it generally exhibits an epoxy value in equivalent per 100 g of derivative higher than or equal to 0.008 and lower than or equal to 1.0.

When the derivative of epichlorohydrin of natural origin is a glycidyl ether, specifically a polyglycidyl ether, more specifically when the polyglycidyl ether is a polymer and most preferably when the polyglycidyl ether is an epoxy resin, it usually exhibits a dynamic viscosity at 25° C. higher than or equal to 50 mPa·s and lower than or equal to 50000.

When the derivative of epichlorohydrin of natural origin is a glycidyl ether, specifically a polyglycidyl ether, more specifically when the polyglycidyl ether is a polymer and most preferably when the polyglycidyl ether is an epoxy resin, it frequently exhibits a content of hydrolysable chloride higher than or equal to 0.01% and lower than or equal to 2.2%.

The invention also relates in a second embodiment to the use of epichlorohydrin of natural origin in the manufacture of a derivative of epichlorohydrin of natural origin, selected from the group consisting of glycidyl ethers presenting an epoxide equivalent weight higher than or equal to 50 g/equivalent and lower than or equal to 15000 g/equivalent, of glycidyl esters, of glycidyl amides, of glycidyl imides, of glycidyl amines, and of any mixture thereof, and of which the $^{14}C$ mass content is such that the ratio $^{14}C/^{12}C$ is higher than $0.70 \times 10^{-12}$.

This use according to the invention generally comprises reacting epichlorohydrin of natural origin with at least one compound comprising at least one active hydrogen atom, wherein the epichlorohydrin of natural origin ratio $^{14}C/^{12}C$ and the said compound ratio $^{14}C/^{12}C$ are such that $$[X_{epi}(^{14}C/^{12}C)_{epi} + X_{cpd}(^{14}C/^{12}C)_{cpd}] > 0.70 \times 10^{-12}$$

wherein
$X_{epi}$ is the fraction of C atoms from epichlorohydrin of natural origin in the derivative of epichlorohydrin of natural origin,
$X_{cpd}$ is the fraction of C atoms from the said compound in the derivative of epichlorohydrin of natural origin,
$(^{14}C/^{12}C)_{epi}$ is the carbon 14 to carbon 12 isotopic ratio in the epichlorohydrin of natural origin,
$(^{14}C/^{12}C)_{cpd}$ is the carbon 14 to carbon 12 isotopic ratio in the said compound.

This use according to the invention presents usually at least one of the following features:
the $(^{14}C/^{12}C)_{epi}$ is higher than or equal to $0.2 \times 10^{-12}$,
$(^{14}C/^{12}C)_{cpd}$ is higher than or equal to $0.2 \times 10^{-12}$.

In the use according to the invention, the $(^{14}C/^{12}C)_{epi}$ ratio is generally higher than or equal to $0.2 \times 10^{-12}$, preferably higher than or equal to $0.4 \times 10^{-12}$, more preferably higher than or equal to $0.6 \times 10^{-12}$, yet more preferably higher than or equal to $0.8 \times 10^{-12}$, still more preferably higher than or equal to $1.1 \times 10^{-12}$ and most preferably equal to $1.2 \times 10^{-12}$. In this last case, all the carbon elements used to manufacture the epichlorohydrin will be of non fossil natural origin.

In the use according to the invention, the $(^{14}C/^{12}C)_{cpd}$ ratio is generally higher than or equal to $0.2 \times 10^{-12}$, preferably higher than or equal to $0.4 \times 10^{-12}$, more preferably higher than or equal to $0.6 \times 10^{-12}$, yet more preferably higher than or equal to $0.8 \times 10^{-12}$, still more preferably higher than or equal to $1.1 \times 10^{-12}$ and most preferably equal to $1.2 \times 10^{-12}$. In this last case, all the carbon elements used to manufacture the said compound will be of non fossil natural origin.

This use according to the invention presents preferably the following features:
the $(^{14}C/^{12}C)_{epi}$ is equal to $1.2 \times 10^{-12}$, and
the $(^{14}C/^{12}C)_{cpd}$ is equal to $1.2 \times 10^{-12}$.

In a very preferred embodiment of the use according to the invention, the $(^{14}C/^{12}C)_{epi}$ ratio and the $(^{14}C/^{12}C)_{cpd}$ ratio are both equal to $1.2 \times 10^{-12}$.

In the use according to the invention, it is preferred that at least one part of the compound containing at least one active hydrogen atom, has been obtained from renewable raw materials. It is more preferred that at least 10% of said compound has been obtained from renewable raw materials, and still more preferred that at least 33% has been obtained from renewable raw materials, yet more preferred that at least 50% has been obtained from renewable raw materials, most preferred at least 75% has been obtained from renewable raw materials, still most preferred that at least 90% has been obtained from renewable raw materials, yet most preferred that at least 95% has been obtained from renewable raw materials, and particularly most preferred that at least 99% has been obtained from renewable raw materials. A compound containing at least one active hydrogen atom of which less than 99.99% has been obtained from renewable raw materials is also suitable. A compound containing at least one active hydrogen atom which has been obtained only from renewable raw materials is particularly convenient.

In the use according to the invention, the at least one compound which reacts with epichlorohydrin contains often at least two active hydrogen atoms, and frequently more than 3 active hydrogen atoms. That compound contains more preferably two active hydrogen atoms. A compound with more than three active hydrogen atoms is also convenient.

In the use according to the invention, the epichlorohydrin of natural origin can be obtained by any process from any starting materials provided that the carbon backbone of at least one part of the epichlorohydrin originates from renewable raw materials and preferably that the carbon backbone of all of the epichlorohydrin originates from renewable raw materials.

The process can be selected from the group consisting of dichloropropanol dehydrochlorination, allyl chloride epoxidation, and combination thereof. It is preferred that at least one part of the epichlorohydrin is obtained by dehydrochlorination of dichloropropanol, preferably by dehydrochlorination of dichloropropanol with a basic compound. The dichloropropanol can be obtained by any process. That process can be selected from the group consisting of allyl chloride hypochlorination, glycerol hydrochlorination, allyl alcohol chlorination, 1,3-dichloroacetone reduction, 2,3-dichloropropanal reduction, and any combination thereof. It is preferred that at least one part of the dichloropropanol is produced by reaction between glycerol and hydrogen chloride. The glycerol can be obtained by any process. That process can be starting from renewable raw materials, fossil raw materials, or any combination thereof. It is preferred that at least one part of said glycerol has been prepared in a conversion process of renewable raw materials.

In one embodiment of the use according to the invention at least one part of the epichlorohydrin of natural origin has been obtained by dehydrochlorination of dichloropropanol, at least one part said dichloropropanol has been produced by reaction between allyl chloride and hypochlorous acid, at least one part of said allyl chloride has been obtained from propylene, and at least one part of said propylene has been prepared in a conversion process of renewable raw materials.

In another embodiment of the use according to the invention, at least one part of the epichlorohydrin of natural origin has been obtained by epoxidation of allyl chloride with hydrogen peroxide, at least one part of said allyl chloride has been obtained from propylene, and at least one part of said propylene has been prepared in a conversion process of renewable raw materials.

In still another embodiment of the use according to the invention, at least one part of the epichlorohydrin of natural origin has been obtained by dehydrochlorination of dichloropropanol, at least one part said dichloropropanol has been produced by chlorination of allyl alcohol, at least one part of said allyl alcohol has been obtained by isomerisation of propylene oxide, at least one part of the propylene oxide has been obtained from propylene, and at least one part of said propylene has been prepared in a conversion process of renewable raw materials.

In a more preferred embodiment of the use according to the invention, at least one part of the epichlorohydrin of natural origin has been obtained by dehydrochlorination of dichloropropanol, at least one part said dichloropropanol has been produced by reaction between glycerol and hydrogen chloride, and at least one part of said glycerol has been prepared in a conversion process of renewable raw materials.

In a most preferred embodiment of the use according to the invention, epichlorohydrin of natural origin has been obtained by dehydrochlorination of dichloropropanol, said dichloropropanol having been produced by reaction between glycerol and hydrogen chloride, and at least one part of said glycerol having been prepared in a conversion process of renewable raw materials.

By glycerol which has been prepared in a conversion process of renewable raw materials, one intends to denote glycerol obtained in the process selected from the group consisting of hydrolysis, saponification, transesterification, aminolysis and hydrogenation of oils and/or fats of animal and/or plant and/or algae origin, of fermentation, hydrogenation and hydrogenolysis of mono- and polysaccharides and derived alcohols, derived from or occurring naturally in the biomass, and any combination thereof.

Glycerol which has been obtained during the manufacture of biodiesel, i.e. during the transesterification of oils and/or fats of animal and/or plant and/or algae, and preferably during the transesterification of oils and/or fats of plant origin, is particularly convenient.

Glycerol which has been obtained in the manufacture of biodiesel is more particularly convenient.

Glycerol which has been obtained during the manufacture of soaps i.e. during the saponification of oils and/or fats of animal and/or plant and/or algae, and preferably during the saponification of oils and/or fats of plant origin, is particularly convenient.

Glycerol which has been obtained in the manufacture of soap is more particularly convenient.

Glycerol which has been obtained during the manufacture of fatty acids i.e. during the hydrolysis of oils and/or fats of animal and/or plant and/or algae, and preferably during the hydrolysis of oils and/or fats of plant origin, is particularly convenient.

Glycerol which has been obtained in the manufacture of fatty acids is more particularly convenient.

Glycerol which has been obtained during the manufacture of fatty alcohols i.e. during the hydrolysis and/or transesterification of oils and/or fats of animal and/or plant and/or algae, and preferably during the hydrolysis and/or transesterification of oils and/or fats of plant origin, is particularly convenient.

Glycerol which has been obtained in the manufacture of fatty alcohols is more particularly convenient.

Glycerol which has been obtained in at least one of the manufacture of soaps, fatty acids and fatty alcohols is more particularly convenient.

In the use according to the invention, the compound containing at least one active hydrogen atom can be of any type. It is preferably selected from the group consisting of a monoalcohol, a polyol, preferably containing more than three carbon atoms, a monocarboxylic acid, a polycarboxylic acid, a monoamine, a polyamine, an amino alcohol, a polyimide, a polyamide, a polyaminoamide, a polyimine, an acid mono- or polyphenol and mixtures of at least two of these compounds.

In the use according to the invention, the polyol, preferably containing more than three carbon atoms, is preferably selected from the group consisting of a polyphenol, a sugar, a polyol derived from a sugar, an acid polyphenol, any derivative thereof, and any mixture thereof.

In the use according to the invention, when the polyol is a polyphenol, the polyphenol is preferably selected from the group consisting of a naturally occurring polyphenol extracted from the cashew nut shell liquid, a lignan, a lignin, a stilbene, a flavonoid, a polyphenol present in the bio-oil from lignin feedstocks, and any mixture thereof.

In the use according to the invention, when the polyphenol is a naturally occurring polyphenol extracted from the cashew nut shell liquid, it is preferably selected from the group consisting of cardanol, cardol, 2-methyl-cardol, and any mixture thereof. In the use according to the invention, when the polyphenol is a lignan, it is preferably selected from the group consisting of pinoresinol, lariciresinol, matairesinol and alpha-conidentrin, and any mixture thereof.

In the use according to the invention, when the polyphenol is a stilbene, it is usually a 1,2-diarylethene with one ring having usually two hydroxyl groups in the meta position and the second ring is substituted by hydroxyl and methoxy groups in the ortho, meta and/or para position. The stilbene is preferably selected from the group consisting of resveratrol, pinosylvin, piceatannol, and any mixture thereof.

In the use according to the invention, when the polyphenol is a flavonoid, it is preferably selected from the group consisting of flavones, flavonols, flavanones, dihydroflavonols and chalcones. The flavonoids are usually in form of monomers, dimers, oligomers and polymers like non hydrolyzable tannins. These polyphenols are preferentially used as a mixture. The polyphenols can also be hydrolyzable tannins like tannic acid, partially hydrolyzed tannins or the polyphenol acids resulting from a complete hydrolysis like gallic acid and ellagic acid. The flavonoid is preferably selected from the group consisting of quercetin, epicatechin, flavan-3,4-diols, and any mixture thereof.

In the use according to the invention, the polyphenol can be present in the bio-oil from lignin feedstocks and it is preferably selected from the group consisting of resorcinol, hydroquinone, catechol, 4-ethyl-catechol, pyrogallol, and any mixture thereof.

In the use according to the invention, when the polyol is a sugar, the sugar is preferably selected from pentoses, hexoses, oligosaccharides, polysaccharides, and any mixture thereof. The hexoses are preferably selected from D-allose, D-altrose, D-glucose, D-mannose, D-gulose, D-idose, D-galactose, D-talose and mixtures thereof. The hexoses are more preferably selected from D-glucose, D-mannose, and mixture thereof.

In the use according to the invention, the sugars can be used as such or after a chemical modification. Such modifications are for example reactions with ethylene oxide, propylene oxide or butylene oxide to produce an oxy alkylated sugar and hydrogenation followed by oxylkylation.

In the use according to the invention, the polyol can be derived from other polyols derivatives prepared from sugars Anhydrosugars like isosorbide, isomannide, isoidide are examples of such polyols. The products of reduction of hydroxymethylfurfural (HMF), 2,4-bis-(hydroxymethyl)-furan and 2,5-bis-(hydroxymethyl)-tetrahydrofuran and more particularly the cis isomer are other examples of such polyols. The hydromethylfurfural can be obtained from hexoses (mainly fructose and glucose) but also from oligosaccharides (e.g. saccharose and cellobiose), from polysaccharides (xylans, chitine, mannans, glucans like starch and cellulose, galactans like agar-agar and fructans like inuline), from lignocellulose and from lignocellulosic biomass.

In the use according to the invention, when the polyol is a product derived from a sugar, the product derived from a sugar is preferably selected from the group consisting of an anhydrosugar, a reduction product from sugar, a reduction product of hydroxymethylfurfural, a difuran derivative of furfural and any mixture thereof.

In the use according to the invention, when the product derived from a sugar is an anhydrosugar, it is preferably selected from the group consisting of isosorbide, isomannide, isoidide and any mixture thereof. The anhydrosugar is more preferably isosorbide.

In the use according to the invention, when the product derived from a sugar is a reduction product from sugar, it is preferably selected from sorbitol, mannitol, xylitol, iditol and any mixture thereof.

In the use according to the invention, when the product derived from a sugar is a reduction product of hydroxymethylfurfural, it is preferably selected from the group consisting of 2,5-bis-(hydroxymethyl)-furan, 2,5-bis-(hydroxymethyl)-tetrahydrofuran, and any mixture thereof.

In the use according to the invention, when the product derived from a sugar is a oxidation product of hydroxymethylfurfural, it is preferably selected from the group consisting of 2,5-furane dicarboxylic acid, 2,5-tetrahydrofuran, dicarboxylic acid and any mixture thereof.

In the use according to the invention, when the product derived from a sugar is a difuran derivative of furfural, it is preferably selected from the group consisting of 5,5'-methylene-bis-2-furanmethanol, 5,5'-isopropylidene-bis-2-furanmethanol, and any mixture thereof.

In the use according to the invention, when the product derived from a sugar is a difuran derivative of furfural, it is preferably selected from the group consisting of 5,5'-methylene-bis-2-furan carboxylic acid, 5,5'-isopropylidene-bis-2-furan carboxylic acid, and any mixture thereof.

In a more preferred embodiment of the use according to the invention, the derivative of epichlorohydrin of natural origin is obtained by reacting epichlorohydrin of natural origin with at least isosorbide.

In the use according to the invention, when the compound containing at least one active hydrogen atom is an acid mono- or polyphenol, it is preferably selected from the group of trans-cinnamic acid mono- or poly-phenol like p-coumaric acid, cafeic acid, ferrulic acid, 5-hydroxy-ferrulic acid, sinapic acid, and mixtures thereof.

In the use according to the invention the compound containing at least one active hydrogen atom can be obtained from lignin containing feedstocks like lignocellulosic biomass feedstocks, lignin-enriched biomass fractions and lignin. The feedstocks can be for example woods like softwood bark, ground softwood, pine, sawdust woodchips, hardwood, mixed hardwoods. Other possible feedstocks are forest residues and agricultural residues like bark waste, peat moss, treetops, limbs, bagasse, bamboo sticks, cashew nut shell, corn bran, cereal straw, coffee husks, stems of corn, *sorghum*, cotton or hemp, reeds, *papyrus*, coconut husks, byproducts from the palm oil production like oil palm fronds, roots, trunks, empty fruit bunch and fiber shells. The feedstocks can also be industrial residues and industrial lignins like lignin from newspaper, paper waste, creosote treated wood waste, birch wood waste, wood industry residues, black pulping liquor, lignin from steam explosion of birch, lignosulphonate, Kraft lignin, hydrolysis lignin, soda lignin, filamentous fungi-treated wood materials, Organosolv lignin, Funaoka lignin and hydrotopic lignin. The lignin containing feedstocks can be used as such. The lignin containing feedstocks can be modified before reaction with epichlorohydrin. The modification is for example esterification with an alcohol, esterification with a mono carboxylic acid or a monoester of a dicarboxylic acid, etherification with an alkylating reagent. The modification can also enhance the reactional ability of the lignin derivatives with epichlorohydrin. Such modifications are for example reactions with ethylene oxide or propylene oxide to produce chain extended hydroxyalkyl lignin, reaction with formaldehyde to produce chain extended hydroxymethyl lignin, reaction with a dicarboxylic acid or an anhydride of a dicarboxylic acid.

In the use according to the invention the compound containing at least one active hydrogen atom can be a phenolics-rich product preferentially produced as bio-oil from the lignin feedstocks described here-above by treatment like slow, fast and flash pyrolysis, hydro-pyrolysis, vacuum pyrolysis, liquefaction and solvolysis (phenol, resorcinol . . . ). The bio-oil can be produced by a catalytic pyrolysis of biomass not containing lignin like vegetable oil or starchy feedstocks. The bio-oil can also be produced by pyrolysis of biosludges (for example biosludges from fructose-manufacturing factory, milk derivative factory or beer brewing factory). The bio-oil contains aliphatic hydrocarbons, acids, esters, alcohols, ketones, aldehydes, furans and phenolics. The phenolics are constituted of phenol, p-cresol, ortho-cresol, meta-cresol, ethyl phenol, 2,3-dimethyl phenol, 2,4-dimethyl phenol, 2,5-dimethyl phenol, 2,6-dimethyl phenol, 3,5-dimethyl phenol, resorcinol, hydroquinone, catechol, 4-ethyl-catechol, pyrogallol, 2-methoxy-4-methyl-phenol, guaiacol, 4-methyl-guaiacol, 4-ethyl-guaiacol, 4-propyl-guaiacol, 4-allyl-guaiacol, 4-(1-propenyl)-guaiacol, syringol, 4-methyl-syringol, 4-ethyl-syringol, 4-allyl-syringol, 4-(1-propenyl)-syringol, 4-hydroxybenzoic acid, 4-hydroxy benzoic acid methyl ester and 3-hydroxy-4-methoxy benzoic acid. The bio-oil can be used as such or can be processed to a purified or enriched phenolics fraction by the means of an additional chemical treatment, a physical fractionation treatment or any combination of these two types of treatment. The additional chemical treatment can be for example an hydrolysis, a dehydration, an hydrogenolysis, an oxydehydroxygenation, etc. The fractionation treatment can be an evaporation, a distillation, a crystallization, an extraction, a chromatography, etc.

In the use according to the invention, when the alcohol is a phenol, it can be used as such or in a mixture. It can also be modified before the reaction with epichlorohydrin of natural origin. The coupling with ketones, the coupling with aldehydes and the oxidative coupling are examples of such modifications. The ketones and aldehydes used can be of non renewable or of renewable origin. Acetone, levulinic acid and formaldehyde are examples of ketones and aldehydes that can be of renewable origin. Levulinic acid is in particular produced from polysaccharides, hemicellulose and glucans, dissacharides or monomeric sugars like glucose and fructose. Diphenolic acid [4,4-bis-(4'-hydroxyphenyl)pentanoic acid] is prepared by the reaction of levulinic acid with two molecules of phenol.

In the use according to the invention, when the compound containing at least one active hydrogen atom is an acid, it is preferably a rosin acids selected from the group consisting of http://en.wikipedia.org/wiki/File:Abietic_acid.svgabietic acid, neoabietic acid, dehydroabietic acid, palustric acid, levopimaric acid, pimaric acid, isopimaric acids, and any mixture thereof and more preferably acids derived from abietic acid and from abietic acid derived imide diacid.

The reaction conditions for the use according to the invention are not critical. The reaction can be carried out under conditions described in prior art for derivatives of epichlorohydrin.

In the use according to the invention it preferred that the epichlorohydrin and the at least one compound comprising at least one active hydrogen atom are both obtained from renewable materials only.

The invention relates in a third embodiment to a process for manufacturing a derivative of epichlorohydrin of natural origin selected from the group consisting of glycidyl ethers presenting an epoxide equivalent weight higher than or equal to 50 g/equivalent and lower than or equal to 15000 g/equivalent, of glycidyl esters, of glycidyl amides, of glycidyl imides, of glycidyl amines, and of any mixture thereof, and of which the $^{14}C$ mass content is such that the ratio $^{14}C/^{12}C$ is higher than $0.7 \times 10^{-12}$, comprising reacting epichlorohydrin of natural origin with at least one compound comprising at least one active hydrogen atom, wherein the epichlorohydrin of natural origin ratio $^{14}C/^{12}C$ and said compound ratio $^{14}C/^{12}C$ are such that $$[X_{epi}(^{14}C/^{12}C)_{epi}+X_{cpd}(^{14}C/^{12}C)_{cpd}] > 0.7 \times 10^{-12}$$

wherein
$X_{epi}$ is the fraction of C atoms from epichlorohydrin of natural origin in the derivative of epichlorohydrin of natural origin,
$X_{cpd}$ is the fraction of C atoms from said compound in the derivative of epichlorohydrin of natural origin,
$(^{14}C/^{12}C)_{epi}$ is the carbon 14 to carbon 12 isotopic ratio in the epichlorohydrin of natural origin, and
$(^{14}C/^{12}C)_{cpd}$ is the carbon 14 to carbon 12 isotopic ratio in said compound.

In a preferred variant of the process according to the invention, the said process presents at least one of the following features:
the $(^{14}C/^{12}C)_{epi}$ is higher than or equal to $0.2 \times 10^{-12}$,
the $(^{14}C/^{12}C)_{cpd}$ is higher than or equal to $0.2 \times 10^{-12}$.

In another preferred variant of the process according to the invention, the $(^{14}C/^{12}C)_{epi}$ in the said process is higher than or equal to $0.2 \times 10^{-12}$.

In still another preferred variant of the process according to the invention, the $(^{14}C/^{12}C)_{cpd}$ is higher than or equal to $0.2 \times 10^{-12}$.

In yet another preferred variant of the process according to the invention, the $(^{14}C/^{12}C)_{epi}$ in the said process is higher than or equal to $0.2 \times 10^{-12}$ and the $(^{14}C/^{12}C)_{cpd}$ is higher than or equal to $0.2 \times 10^{-12}$.

In a more preferred variant of the process according to the invention, the said process presents the following features:
the $(^{14}C/^{12}C)_{epi}$ is equal to $1.2 \times 10^{-12}$, and
the $(^{14}C/^{12}C)_{cpd}$ is equal to $1.2 \times 10^{-12}$.

Detailed information concerning the derivative of epichlorohydrin of natural origin, natural epichlorohydrin, the compound comprising at least one active hydrogen atom, as well as preferred embodiments concerning the process, can be taken from the previous detailed description relating to the product and the use in accordance with the instant invention, to which reference is made.

The processes for preparing the derivative of epichlorohydrin, dichloropropanol and epichlorohydrin can be such as disclosed in US issued patent or patent applications U.S. Pat. Nos. 8,415,509, 8,173,823, 8,067,645, 893,193, 2008-0200701, U.S. Pat. Nos. 7,906,692, 7,615,670, 7,906,691, 8,344,185, 7,939,696, 2008-0194850, 8,106,245, 7,557,253, 8,389,777, 2008-0214848, 8,124,814, 8,258,350, 2010-0032617, U.S. Pat. Nos. 8,273,923, 8,471,074, 8,399,692, 8,197,665, 2010-0179302, U.S. Pat. Nos. 8,715,568, 8,507,643, 8,378,130, 8,314,205, 2011-0237773, 2011-0152545, and U.S. Pat. No. 8,536,381 filed in the name of SOLVAY, the contents of which are incorporated herein by reference.

The invention relates in a fourth embodiment to the use of a derivative of epichlorohydrin of natural origin, selected from the group consisting of glycidyl ethers presenting an epoxide equivalent weight higher than or equal to 50 g/equivalent and lower than or equal to 15000 g/equivalent, of glycidyl esters, of glycidyl amides, of glycidyl imides, of glycidyl amines, and any mixture thereof, of which the $^{14}C$ mass content is such that the ratio $^{14}C/^{12}C$ is higher than $0.7 \times 10^{-12}$, more specifically as raw materials in the production of coatings or composites. In that use, the derivative of epichlorohydrin of natural origin and the process for making that product are as described here above.

In a first aspect of that fourth embodiment, the coating obtained from derivative of epichlorohydrin of natural origin can be used in the fields of marine and industrial maintenance, of metal container, of coil coatings, of automotive coatings or of inks and resists.

The coating obtained from derivative of epichlorohydrin of natural origin can be used in the fields of marine and industrial maintenance (corrosion-resistant coatings for ships, shipping containers, offshore oil rigs and platforms, transportation infrastructures such as bridges, rail car coatings, coatings for industrial storage tanks, and primers for light industrial and agricultural equipment), of metal container (aluminum and steel food and beverage cans), of coil coatings (metal can ends, can bodies, building products, appliance panels, transportation, and metal furniture applications), of automotive coatings (primer surface coatings) and of inks and resists. Coating can be done using various technologies like low solids solvent borne coating, high solid solvent borne coating, solvent-free coating, waterborne coating, powder coating and radiation-curable coating.

In a first preferred variant of that first aspect the use of a derivative of epichlorohydrin of natural origin is in the production of coatings for marine and industrial maintenance comprising corrosion-resistant coatings for ships, shipping containers, offshore oil rigs and platforms, transportation infrastructures such as bridges, rail car coatings, coatings for industrial storage tanks, and primers for light industrial and/or agricultural equipment In a second preferred variant of that first aspect, the use of a derivative of epichlorohydrin of natural origin is in the production of coatings for metal containers comprising aluminum and steel food and beverage cans.

In a third preferred variant of that first aspect, the use of a derivative of epichlorohydrin of natural origin is in the production of coatings for coils coatings comprising metal can ends, can bodies, building products, appliance panels, transportation, and metal furniture applications.

In a fourth preferred variant of that first aspect, the use of a derivative of epichlorohydrin of natural origin is in the production of coatings for automotive coatings comprising primer surface coatings.

In a fifth preferred variant of that first aspect, the use of a derivative of epichlorohydrin of natural origin is in the production of coatings for inks and resists.

In a second aspect of that fourth embodiment, the composites can be used in the field of structural composites (fiber reinforcing materials based on glass, boron, graphite, aromatic polyaramides and natural fibers). The natural fibers can be of vegetable or of animal origin. The vegetable fibers can be bast fibers, leaf fibers, seed-hair fibers, grass fibers, straw fibers, root fibers or wood fibers. Bast fibers are produced for example by Flax, Hemp, Jute, Banana, China jute, Kenaf, Kudzu, Nettle, Paper Mulberry, *Papyrus*, Pennywort, Ramie, Roselle, Seagrasses, Sunn hemp, *Arundo Donax*, Elephant Grass, Bamboo, Urena, Sunflower, Water Hyacinth and bagasse from Sugar Cane and *Sorghum*. Leaf fibers are produced for example by Abaca, Cantala, Caroa, Corn, Curaua, Fique, Henequen, Istle, Mauritius, Phormium, Pineapple, Sanseviera, Sisal, palm trees like Gomuti, Palmyra Palm, Piassava, Crin vegetal and Raffia. Seed-hair fibers are produced for example by African Palm, Coir, Cotton, Kapok and Milkweed floss. Grass fibers are produced for example by Alfalfa, Babhar grass, Esparto, Reed Canary grass, Sabai grass, switchgrass and *Miscanthus*. Straw fibers are produced for example by barley, rice, oat, rye and wheat. Root fibers are produced for example by Cassava and Broom root. The wood fibers can be issued from soft or hard wood. The animal fibers can be for example poultry feather, silk and wool.

In that second aspect, the composites can also be used in the field of civil engineering of flooring (floor paints, self-leveling floors, trowelable floors, and pebble-finished floors) and of construction, of electrical laminates (printed wiring boards and printed circuit boards), of other electrical and electronic applications, like casting, potting, encapsulation (switchgear components, transformers, insulators, high voltage cable accessories, and similar devices) and transfer molding (encapsulation of electronic components such as semiconductor chips, passive devices, and integrated circuits), of adhesives (cohesion between similar and dissimilar materials such as metals, glass, ceramics, wood, cloth, and many types of plastics) and of tooling (prototypes, master models, molds and other parts for aerospace, automotive, foundry, boat building, and various industrial molded items)

In a first preferred variant of that second aspect, the use of a derivative of epichlorohydrin of natural origin is in the fields of structural composites, of civil engineering, of flooring, of construction, of electrical laminates, of electrical and electronic applications, of transfer molding, of adhesives, of energy production or of tooling.

In a second preferred variant of that second aspect, the use of a derivative of epichlorohydrin of natural origin is in the production of composites for structural composites comprising fiber reinforcing materials based on glass, boron, graphite, aromatic polyaramides and/or natural fibers.

In a third preferred variant of that second aspect, the use of a derivative of epichlorohydrin of natural origin is in the production of composites for civil engineering comprising for instance adhesives. The adhesives applications are for example in the fields of air field runways and aprons, highway and bridge joints, bridge abutments, concrete lined canals, traverse and longitudinal joints, multilevel parking lot joints, underground tunnel construction joints and sections, attaching metal studs in concrete, bonding traffic markers on roadways and road dividers, bonding pancake lighting systems in airport runways, parking lots, etc. In a fourth preferred variant of that second aspect, the use of a derivative of epichlorohydrin of natural origin is in the production of composites for flooring comprising floor paints, self-leveling floors, trowelable floors, and/or pebble-finished floors.

In a fifth preferred variant of that second aspect, the use of a derivative of epichlorohydrin of natural origin is in the production of composites for construction comprising among others adhesives applications and formed parts, obtained for instance by extrusion, pultrusion and any other forming techniques.

In a sixth preferred variant of that second aspect, the use of a derivative of epichlorohydrin of natural origin is in the production of composites for energy production comprising windmill blade and/or turbine housing.

In a seventh preferred variant of that second aspect, the use of a derivative of epichlorohydrin of natural origin is in the production of composites for electrical laminates comprising printed wiring boards and/or printed circuit boards.

In an eighth first preferred variant of that second aspect, the use of a derivative of epichlorohydrin of natural origin is in the production of composites for electrical and electronic applications compring switchgear components, transformers, insulators, high voltage cable accessories, and/or similar devices.

In a ninth preferred variant of that second aspect, the use of a derivative of epichlorohydrin of natural origin is in the production of composites for transfer molding comprising the encapsulation of electronic components such as semiconductor chips, passive devices, and/or integrated circuits.

In a tenth preferred variant of that second aspect, the use of a derivative of epichlorohydrin of natural origin is in the production of composites for adhesive for cohesion between similar and dissimilar materials such as metals, glass, ceramics, wood, cloth, and many types of plastics.

In a eleventh preferred variant of that second aspect, the use of a derivative of epichlorohydrin of natural origin is in the production of composites for tooling comprising prototypes, master models, molds and/or other parts for aerospace, automotive, foundry, boat building, and/or various industrial molded items.

The examples below are intended to illustrate the invention without, however, limiting it.

Example 1 (Not According the Invention)

The apparatus employed was a thermostatised flask equipped with a mechanical stirrer, with a jacket containing a thermocouple and with a Dean-Stark separator surmounted by a water-cooled condenser. A pump has been used to inject a caustic soda aqueous solution at a constant rate in the flask.

The reaction flask has initially been loaded with a mixture of isosorbide (43.8 g, 0.3 mol) and the epichlorohydrin sample ECH1 coming from a propylene-chlorine plant (275.0 g, 3.0 mol). The epichlorohydrin ECH1 has been obtained by dehydrochlorination of dichloropropanol, the dichloropropanol having been obtained by hypochlorination of allyl chloride, the allyl chloride having been obtained by chlorination of propylene, a fossil raw material. The analysis of the epichlorohydrin ECH 1 is given in Table 1. The mixture has been heated at reflux under stirring to a temperature of 115° C. A 50% aqueous solution of caustic soda (49.8 g, 0.6 mol) has been introduced at a rate of 3.276 ml/h during 10 hour. The temperature of the mixture in the flask has been maintained in the range 100° C.-115° C. in order to assure a constant reflux. The epichlorohydrin rich organic phase which decanted during the reaction as a lower phase in the separator has been recycled regularly in the reaction flask and the aqueous rich phase collected as an upper phase in the separator has been regularly drawn off. The heating has been maintained for 15 min after the total introduction of the caustic soda solution to achieve the collect of the water phase in the decantor. 33.0 g of aqueous phase (W1) have been collected with a composition given in Table 1.

The epichlorohydrin in excess has been removed from the reaction mixture by distillation under a vacuum of 30 torr and by a progressive heating of the mixture to 107° C. 199.7 g (2.1 mol) of epichlorohydrin have been recovered in this step. The composition of the distillate (ECH2) is given in Table 1.

The salt has been separated from the crude product (40.3 g) after addition of 78.0 g of acetone under agitation and by filtration. The cake of filtration has been washed with 50.0 ml of acetone. The acetone solutions have been mixed and evaporated at 60° C. under a pressure of 20 torr.

The residual product of the evaporation (75.9 g) contained less than 1% g/g of unconverted isosorbide. The residue contained 0.450 mol epoxy per 100 g and 0.32% of hydrolysable chlorine.

The residual product had a $^{14}C$ mass content such that the ratio $^{14}C/^{12}C$ was $0.64\times10^{-12}$ (measured according to standard ASTM D6866).

Example 2 (According the Invention)

The trial has been carried out in the apparatus described in example 1.

The reaction flask has been initially charged with a mixture of isosorbide (43.8 g, 0.3 mol) and epichlorohydrin sample ECH 3 (278 g, 3.0 mol). The epichlorohydrin ECH3 has been obtained by dehydrochlorination of dichloropropanol, the dichloropropanol having been obtained by hydrochlorination of natural glycerol, the glycerol having been obtained from renewable raw materials. The analysis of the epichlorohydrin is given in Table 1. The mixture has been heated at reflux under stirring to a temperature of 115° C. A 50% aqueous solution of caustic soda (49.8 g, 0.6 mol) has been introduced at a rate of 3.276 ml/h during 10 hour. The temperature of the mixture in the flask has been maintained in the range 104° C.-115° C. in order to assure a constant reflux. The epichlorohydrin rich organic phase which decanted during the reaction as a lower phase in the separator has been recycled regularly in the reaction flask and the aqueous rich phase collected as an upper phase in the separator was regularly drawn off. The heating has been maintained for 15 min after the total introduction of the caustic soda solution to achieve the collect of the water phase in the decantor. 33.5 g of aqueous phase (W2) have been collected with a composition given in Table 1.

The epichlorohydrin in excess has been removed from the reaction mixture by distillation under a vacuum of 40 torr and by a progressive heating of the mixture to 70° C. 202.1 g (2.2 mol) of epichlorohydrin has been recovered in this step. The composition of the distillate (ECH4) is given in Table 1.

The salt has been separated from the crude product (38.4 g) after addition of 78 g of acetone under agitation and by filtration. The cake of filtration has been washed with 50 ml of acetone. The acetone solutions have been mixed and evaporated at 60° C. under a pressure of 20 torr.

The residual product of the evaporation (73.8 g) contained less than 1% g/g of unconverted isosorbide. The residue contained 0.457 mol epoxy per 100 g and 0.16% of hydrolysable chlorine.

The residual product had a $^{14}C$ mass content such that the ratio $^{14}C/^{12}C$ was $1.2\times10^{-12}$ (measured according to standard ASTM D6866).

The High Performance Liquid Chromatography analyses of the residual products obtained in examples 1 and 2 are presented in Table 1.

TABLE 1

| | Example 1 | | | Example 2 | | |
|---|---|---|---|---|---|---|
| Component | ECH1 (g/kg) | ECH2 (g/kg) | W1 (mg/l) | ECH3 (g/kg) | ECH4 (g/kg) | W2 (mg/l) |
| acetaldehyde | n.d. | n.d | 0.39 | n.d | n.d | 0.4 |
| acrolein | n.d | n.d | 0.06 | n.d | n.d | 0.07 |
| 2-propanol | n.d | n.d | <0.05 | n.d | n.d | n.d |
| allyl alcohol | 0.002 | n.d | 0.28 | 0.005 | 0.003 | 0.28 |
| hydroxyacetone | 0.012 | 0.004 | n.d | 0.006 | 0.006 | n.d |
| chloroacetone + (3,3-dichloro-1-propene) | 0.003 | n.d | n.d | 0.041 | 0.003 | n.d |
| 1,2-dichloropropane | 0.019 | 0.011 | n.d | 0.003 | n.d | n.d |
| 2,3-dichloro-1-propene | 0.006 | 0.031 | n.d | n.d | n.d | n.d |
| 1-chloro-2,3-epoxypropane | Principal product | Principal product | (7.2g/kg) | Principal product | Principal product | (11g/kg) |
| 1,3-dichloro-1-propene cis maj. + (C6H14O min.) | 0.041 | 0.030 | n.d | 0.001 | n.d | n.d |
| 2-chloro-2-propene-1-ol | 0.14 | 0.016 | n.d | 0.020 | 0.006 | 0.05 |
| 1,3-dichloro-1-propene trans | 0.014 | 0.01 | n.d | 0.009 | 0.006 | |
| $C_5H_{10}O/C_4H_7ClO$ | 0.006 | 0.008 | n.d | n.d | n.d | n.d |
| $C_6H_{12}O$ | n.d | n.d | 0.17 | n.d | n.d | 0.16 |
| 1,3-dichloropropane + Ni | 0.002 | 0.001 | 0.09 | 0.024 | 0.028 | 0.09 |

TABLE 1-continued

|  | Example 1 | | | Example 2 | | |
| --- | --- | --- | --- | --- | --- | --- |
| Component | ECH1 (g/kg) | ECH2 (g/kg) | W1 (mg/l) | ECH3 (g/kg) | ECH4 (g/kg) | W2 (mg/l) |
| Cyclopentanone | n.d | n.d | n.d | 0.009 | 0.011 | n.d |
| dibromochloromethane | 0.019 | n.d | n.d | n.d | n.d | n.d |
| $C_6H_{10}O$ iso 1 | 0.007 | 0.007 |  | n.d | n.d | n.d |
| $C_6H_{10}O$ iso 2 | 0.026 | 0.03 | 0.16 | n.d | n.d | 0.15 |
| 1,2-epoxyhexane + (1,2,2-trichloropropane) | 0.011 | 0.013 | n.d | n.d | n.d | n.d |
| $C_6H_{10}O$ iso 3 | 0.013 | 0.016 | n.d | n.d | n.d | n.d |
| dichloroepoxypropane + Ni | 0.012 | 0.005 | n.d | n.d | n.d | n.d |
| 1,3,3-trichloro-1-propene cis + 1,1,3-trichloropropene | 0.006 | n.d | n.d | n.d | n.d | n.d |
| 1,1,2-trichloropropane | 0.041 | n.d | n.d | 0.003 | 0.031 | n.d |
| chlorobenzène | 0.015 | 0.019 | n.d | 0.003 | 0.003 | n.d |
| 1,3,3-trichloro-1-propene trans | 0.013 | n.d | n.d | n.d | n.d | n.d |
| 1,2,3-trichloropropene trans | 0.003 | n.d | n.d | n.d | n.d | n.d |
| 1,3-dichloro-2-propanol | 0.01 | 0.1 | 0.59 | 0.014 | 0.11 | 0.3 |
| 1,2,3-trichloropropane | 0.046 | n.d | n.d | n.d | n.d | n.d |
| 3-chloro-1,2-propanediol + 2,3-dichloro-1-propanol | 0.005 | 0.01 | 95 g/kg | 0.019 | n.d | 84 g/kg |
| $C_6H_{13}Br$ |  |  | n.d | n.d | n.d | n.d |
| $C_6H_{10}Cl_2$ iso 1 | 0.012 | 0.014 | n.d | n.d | n.d | n.d |
| $C_6H_{10}Cl_2$ iso 2 | 0.009 | 0.011 | n.d | n.d | n.d | n.d |
| methyl glycidyl ether | n.d | n.d | n.d | 0.006 | 0.007 | n.d |
| glycidol | n.d | 2.6 | n.d | 0.002 | 2.7 | n.d |
| glycerol | n.d | 0.11 | n.d | n.d | 0.13 | n.d |
| Unknowns (sum) | 0.109 | 0.995 | 0.62 | 0.02 | 0.584 | 0.63 | n.d.: not detected n.i.: unidentified product

The invention claimed is:

1. A derivative of natural origin, selected from the group consisting of glycidyl ethers,
   wherein said glycidyl ethers present an epoxide equivalent weight higher than or equal to 50 g/equivalent and lower than or equal to 15000 g/equivalent, and
   wherein said derivative is obtained from epichlorohydrin of natural origin and from at least one compound containing at least one active hydrogen atom, at least one part of said compound having been obtained from renewable raw materials, the natural origin of the derivative resulting in a $^{14}C$ mass content of said derivative which is such that the ratio of $^{14}C/^{12}C$ is higher than $0.7 \times 10^{-12}$.

2. The derivative of natural origin according to claim 1 wherein said glycidyl ether further exhibits characteristics selected from the group consisting of
   an epoxy value in equivalent per 100 g of derivative higher than or equal to 0.008 and lower than or equal to 1.0,
   a dynamic viscosity at 25° C. higher than or equal to 50 mPa·s and lower than or equal to 50000, a content of hydrolysable chloride higher than or equal to 0.01% and lower than or equal to 2.2%, and any combination thereof.

3. The derivative of natural origin according to claim 2 wherein said glycidyl ether exhibits an epoxy value in equivalent per 100 g of derivative higher than or equal to 0.008 and lower than or equal to 1.0.

4. The derivative of natural origin according to claim 2 wherein said glycidyl ether exhibits a dynamic viscosity at 25° C. higher than or equal to 50 mPa·s and lower than or equal to 50000.

5. The derivative of natural origin according to claim 2 wherein said glycidyl ether exhibits a content of hydrolysable chloride higher than or equal to 0.01% and lower than or equal to 2.2%.

6. The derivative of natural origin according to claim 1 wherein said glycidyl ether is a polyglycidyl ether.

7. The derivative of natural origin according to claim 6 wherein said polyglycidyl ether is a polyglycidyl ether polymer.

8. The derivative of natural origin according to claim 1, wherein the $^{14}C$ mass content of said derivative of natural origin is such that the ratio $^{14}C/^{12}C$ is equal to $1.2 \times 10^{-12}$.

9. A method for using a derivative of epichlorohydrin of natural origin according to claim 1.

10. A process for manufacturing the derivative of natural origin according to claim 1 comprising reacting epichlorohydrin of natural origin with at least one compound having at least one active hydrogen atom, at least one part of said compound having been obtained from renewable raw materials.

11. The process according to claim 10, wherein said epichlorohydrin ratio $^{14}C/^{12}C$ and said compound ratio $^{14}C/^{12}C$ are such that $$[X_{epi}(^{14}C/^{12}C)_{epi} + X_{cpd}(^{14}C/^{12}C)_{cpd}] > 0.7 \times 10^{-12}$$

wherein $X_{epi}$ is the fraction of C atoms from epichlorohydrin in said derivative of natural origin,
$X_{cpd}$ is the fraction of C atoms from said compound in said derivative of natural origin,
$(^{14}C/^{12}C)_{epi}$ is the carbon 14 to carbon 12 isotopic ratio in said epichlorohydrin, and
$(^{14}C/^{12}C)_{cpd}$ is the carbon 14 to carbon 12 isotopic ratio in said compound.

12. The process according to claim 11
    wherein the $(^{14}C/^{12}C)_{epi}$ is higher than or equal to $0.2 \times 10^{-12}$, and
    wherein the $(^{14}C/^{12}C)_{cpd}$ is higher than or equal to $0.2 \times 10^{-12}$.

13. The process according to claim 12 wherein the $(^{14}C/^{12}C)_{epi}$ s equal to $1.2 \times 10^{-12}$, and wherein the $(^{14}C/^{12}C)_{cpd}$ is equal to $1.2 \times 10^{-12}$.

14. The process according to claim 11, wherein said epichlorohydrin is obtained by dehydrochlorination of dichloropropanol, said dichloropropanol is produced by reaction between glycerol and hydrogen chloride,
- wherein at least one part of said glycerol is prepared in a conversion process of renewable raw materials, or obtained in the manufacture of biodiesel, or obtained in at least one of the manufacture of soaps, fatty acids and fatty alcohols,
- wherein said conversion process of renewable raw materials is selected from the group consisting of hydrolysis, saponification, transesterification, aminolysis and hydrogenation of oils and/or fats of animal, plant and/or algae, fermentation, hydrogenation, and hydrogenolysis of mono- and polysaccharides and alcohols occurring naturally in the biomass, and any combination thereof.

15. The process according to claim 11, wherein at least one part of said compound having at least one active hydrogen atom is obtained from renewable raw materials, and
- wherein the compound having at least one active hydrogen atom is selected from the group consisting of a monoalcohol, a polyol having more than three carbon atoms, an amino alcohol, an acid mono- or polyphenol and any mixture thereof, and
- wherein said polyol contains more than three carbon atoms is selected from the group consisting of a polyphenol, a sugar, a polyol derived from a sugar, an acid polyphenol, and any mixture thereof, and
- wherein said polyol derived from a sugar is selected from the group consisting of an anhydrosugar, a reduction product from a sugar, a reduction product of hydroxymethylfurfural, a difuran derivative of furfural, and any mixture thereof, and
- wherein said difuran derivative of furfural is selected from the group consisting of 5,5'-methylene-bis-2-furanmethanol, 5,5'-isopropylidene-bis-2-furanmethanol, and any mixture thereof.

16. The process according to claim 15 wherein said anhydrosugar is selected from the group consisting of isosorbide, isomannide, isoidide and any mixture thereof.

17. The process according to claim 16 wherein the anhydrosugar is isosorbide.

* * * * *